United States Patent
Bahney

(10) Patent No.: US 8,348,948 B2
(45) Date of Patent: Jan. 8, 2013

(54) VESSEL SEALING SYSTEM USING CAPACITIVE RF DIELECTRIC HEATING

(75) Inventor: Timothy J. Bahney, Boulder, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 0 days.

(21) Appl. No.: 12/846,602

(22) Filed: Jul. 29, 2010

(65) Prior Publication Data

US 2010/0312235 A1    Dec. 9, 2010

Related U.S. Application Data

(62) Division of application No. 11/063,684, filed on Feb. 23, 2005, now Pat. No. 7,780,662.

(60) Provisional application No. 60/549,232, filed on Mar. 2, 2004.

(51) Int. Cl.
*A61B 18/14* (2006.01)
(52) U.S. Cl. ............... 606/51; 606/32; 606/40
(58) Field of Classification Search ......... 606/51, 606/52, 32, 40
See application file for complete search history.

(56) References Cited

U.S. PATENT DOCUMENTS

| | | |
|---|---|---|
| 371,664 A | 10/1887 | Brannan et al. |
| 1,586,645 A | 6/1926 | Bierman |
| 1,813,902 A | 7/1931 | Bovie |
| 1,822,330 A | 9/1931 | Ainslie |
| 1,852,542 A | 4/1932 | Sovatkin |
| 1,908,201 A | 5/1933 | Welch et al. |
| 2,002,594 A | 5/1935 | Wappler et al. |
| 2,011,169 A | 8/1935 | Wappler |
| 2,031,682 A | 2/1936 | Wappler et al. |
| 2,054,149 A | 9/1936 | Wappler |
| 2,176,479 A | 10/1939 | Willis |
| 2,305,156 A | 4/1941 | Grubel |
| 2,279,753 A | 4/1942 | Knopp |
| 2,327,353 A | 8/1943 | Karle |
| 2,632,661 A | 8/1948 | Cristofv |
| 2,668,538 A | 2/1954 | Baker |
| 2,796,065 A | 6/1957 | Kapp |
| 3,073,311 A | 1/1963 | Tibbs et al. |
| 3,100,489 A | 8/1963 | Bagley |
| 3,372,288 A | 3/1968 | Wigington |

(Continued)

FOREIGN PATENT DOCUMENTS

CA    2 104 423    2/1994

(Continued)

OTHER PUBLICATIONS

U.S. Appl. No. 09/387,883, filed Sep. 1, 1999.

(Continued)

*Primary Examiner* — Lee S Cohen

(57) ABSTRACT

An electrosurgical system for sealing vessels using capacitive (RF) dielectric heating and a method thereof are provided. The system includes an electrosurgical instrument having an end effector with parallel plate electrodes that will clamp onto a vessel and maintain a specified gap distance; however, the electrodes will be coated with a non-conductive dielectric material. Such an end effector will ensure that direct conduction between the electrodes does not occur through tissue or fluids and effectively creates a parallel plate capacitor with a dielectric, e.g., tissue and coating, in between the plates. The electrosurgical instrument will be activated with an AC signal at a specified RF frequency, e.g., a Debye resonance frequency, via an electrosurgical generator. An effective AC current will flow through the tissue and cause heating due to fictional losses from rotating polar molecules in the tissue.

10 Claims, 7 Drawing Sheets

U.S. PATENT DOCUMENTS

| | | |
|---|---|---|
| 3,459,187 A | 8/1969 | Pallotta |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,801,766 A | 4/1974 | Morrison, Jr. |
| 3,862,630 A | 1/1975 | Balamuth |
| 3,863,339 A | 2/1975 | Reaney et al. |
| 3,866,610 A | 2/1975 | Kletschka |
| 3,875,945 A | 4/1975 | Friedman |
| 3,897,786 A | 8/1975 | Garnett et al. |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| D249,549 S | 9/1978 | Pike |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,200,104 A | 4/1980 | Harris |
| 4,233,734 A | 11/1980 | Bies |
| 4,236,470 A | 12/1980 | Stenson |
| 4,274,413 A | 6/1981 | Hahn et al. |
| 4,300,564 A | 11/1981 | Furihata |
| 4,311,145 A | 1/1982 | Esty et al. |
| D263,020 S | 2/1982 | Rau, III |
| 4,315,510 A | 2/1982 | Kihn |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,513,271 A | 4/1985 | Reisem |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,619,258 A | 10/1986 | Pool |
| 4,624,254 A | 11/1986 | McGarry et al. |
| 4,644,950 A | 2/1987 | Valli |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,674,499 A | 6/1987 | Pao |
| 4,685,459 A | 8/1987 | Xoch et al. |
| 4,733,662 A | 3/1988 | DeSatnick et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| D298,353 S | 11/1988 | Manno |
| D299,413 S | 1/1989 | DeCarolis |
| 4,805,616 A | 2/1989 | Pao |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,890,610 A | 1/1990 | Kirwan, Sr. et al. |
| 4,938,761 A | 7/1990 | Ensslin |
| 4,947,009 A | 8/1990 | Osika et al. |
| 4,985,030 A | 1/1991 | Melzer et al. |
| 5,007,908 A | 4/1991 | Rydell |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,122,139 A | 6/1992 | Sutter |
| 5,147,357 A | 9/1992 | Rose et al. |
| 5,151,102 A | 9/1992 | Kamiyama et al. |
| 5,151,978 A | 9/1992 | Bronikowski et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,269,804 A | 12/1993 | Bales et al. |
| D343,453 S | 1/1994 | Noda |
| 5,275,615 A | 1/1994 | Rose |
| 5,277,201 A | 1/1994 | Stern |
| 5,281,220 A | 1/1994 | Blake, III |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,300,082 A | 4/1994 | Sharpe et al. |
| 5,304,203 A | 4/1994 | El-Mallawany et al. |
| 5,308,353 A | 5/1994 | Beurrier |
| 5,308,357 A | 5/1994 | Lichtman |
| 5,313,027 A | 5/1994 | Inoue et al. |
| 5,314,445 A | 5/1994 | Degwitz et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| 5,330,502 A | 7/1994 | Hassler et al. |
| D349,341 S | 8/1994 | Lichtman et al. |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,350,391 A | 9/1994 | Iacovelli |
| 5,352,222 A | 10/1994 | Rydell |
| 5,354,271 A | 10/1994 | Voda |
| 5,356,408 A | 10/1994 | Rydell |
| 5,359,993 A | 11/1994 | Slater et al. |

| | | | | | |
|---|---|---|---|---|---|
| 5,366,477 A | 11/1994 | LeMarie, III et al. | 5,549,604 A | 8/1996 | Sutcu et al. |
| 5,367,250 A | 11/1994 | Whisenand | 5,558,671 A | 9/1996 | Yates |
| 5,368,600 A | 11/1994 | Failla et al. | 5,558,672 A | 9/1996 | Edwards et al. |
| 5,374,277 A | 12/1994 | Hassler | 5,562,619 A | 10/1996 | Mirarchi et al. |
| 5,376,089 A | 12/1994 | Smith | 5,562,699 A | 10/1996 | Heimberger et al. |
| 5,376,094 A | 12/1994 | Kline | 5,562,720 A | 10/1996 | Stern et al. |
| D354,564 S | 1/1995 | Medema | 5,564,615 A | 10/1996 | Bishop et al. |
| 5,383,875 A | 1/1995 | Bays et al. | 5,569,241 A | 10/1996 | Edwardds |
| 5,383,880 A | 1/1995 | Hooven | 5,569,243 A | 10/1996 | Kortenbach et al. |
| 5,383,897 A | 1/1995 | Wholey | 5,571,100 A | 11/1996 | Goble et al. |
| 5,389,098 A | 2/1995 | Tsuruta et al. | 5,573,424 A | 11/1996 | Poppe |
| 5,389,103 A | 2/1995 | Melzer et al. | 5,573,534 A | 11/1996 | Stone |
| 5,389,104 A | 2/1995 | Hahnen et al. | 5,573,535 A | 11/1996 | Viklund |
| 5,391,166 A | 2/1995 | Eggers | 5,575,799 A | 11/1996 | Bolanos et al. |
| 5,391,183 A | 2/1995 | Janzen et al. | 5,575,805 A | 11/1996 | Li |
| 5,395,360 A | 3/1995 | Manoukian | 5,578,052 A | 11/1996 | Koros et al. |
| 5,396,900 A | 3/1995 | Slater et al. | 5,579,781 A | 12/1996 | Cooke |
| 5,403,312 A | 4/1995 | Yates et al. | 5,582,611 A | 12/1996 | Tsukagoshi et al. |
| 5,403,342 A | 4/1995 | Tovey et al. | 5,582,617 A | 12/1996 | Klieman et al. |
| 5,405,344 A | 4/1995 | Williamson et al. | 5,585,896 A | 12/1996 | Yamazaki et al. |
| 5,409,763 A | 4/1995 | Serizawa et al. | 5,590,570 A | 1/1997 | LeMaire, III et al. |
| D358,887 S | 5/1995 | Feinberg | 5,591,181 A | 1/1997 | Stone et al. |
| 5,411,519 A | 5/1995 | Tovey et al. | 5,597,107 A | 1/1997 | Knodel et al. |
| 5,411,520 A | 5/1995 | Nash et al. | 5,599,350 A | 2/1997 | Schulze et al. |
| 5,413,571 A | 5/1995 | Katsaros et al. | 5,601,224 A | 2/1997 | Bishop et al. |
| 5,415,656 A | 5/1995 | Tihon et al. | 5,601,601 A | 2/1997 | Tal et al. |
| 5,415,657 A | 5/1995 | Taymor-Luria | 5,601,641 A | 2/1997 | Stephens |
| 5,417,709 A | 5/1995 | Slater | 5,603,711 A | 2/1997 | Parins et al. |
| 5,422,567 A | 6/1995 | Matsunaga | 5,603,723 A | 2/1997 | Aranyi et al. |
| 5,423,810 A | 6/1995 | Goble et al. | 5,607,436 A | 3/1997 | Pratt et al. |
| 5,425,690 A | 6/1995 | Chang | 5,611,798 A | 3/1997 | Eggers |
| 5,425,739 A | 6/1995 | Jessen | 5,611,808 A | 3/1997 | Hossain et al. |
| 5,429,616 A | 7/1995 | Schaffer | 5,611,813 A | 3/1997 | Lichtman |
| 5,431,672 A | 7/1995 | Cote et al. | 5,620,415 A | 4/1997 | Lucey et al. |
| 5,431,674 A | 7/1995 | Basile et al. | 5,620,453 A | 4/1997 | Nallakrishnan |
| 5,437,292 A | 8/1995 | Kipshidze et al. | 5,620,459 A | 4/1997 | Lichtman |
| 5,438,302 A | 8/1995 | Goble | 5,624,452 A | 4/1997 | Yates |
| 5,439,478 A | 8/1995 | Palmer | 5,626,578 A | 5/1997 | Tihon |
| 5,441,517 A | 8/1995 | Kensey et al. | 5,626,607 A | 5/1997 | Malecki et al. |
| 5,443,463 A | 8/1995 | Stern et al. | 5,626,609 A | 5/1997 | Zvenyatsky et al. |
| 5,443,464 A | 8/1995 | Russell et al. | 5,630,833 A | 5/1997 | Katsaros et al. |
| 5,443,480 A | 8/1995 | Jacobs et al. | 5,637,110 A | 6/1997 | Pennybacker et al. |
| 5,445,638 A | 8/1995 | Rydell et al. | 5,638,003 A | 6/1997 | Hall |
| 5,445,658 A | 8/1995 | Durrfeld et al. | 5,639,403 A | 6/1997 | Ida et al. |
| 5,449,480 A | 9/1995 | Kuriya et al. | 5,643,294 A | 7/1997 | Tovey et al. |
| 5,451,224 A | 9/1995 | Goble et al. | 5,647,869 A | 7/1997 | Goble et al. |
| 5,454,809 A | 10/1995 | Janssen | 5,647,871 A | 7/1997 | Levine et al. |
| 5,454,823 A | 10/1995 | Richardson et al. | 5,649,959 A | 7/1997 | Hannam et al. |
| 5,454,827 A | 10/1995 | Aust et al. | 5,655,650 A | 8/1997 | Naitou |
| 5,456,684 A | 10/1995 | Schmidt et al. | 5,658,281 A | 8/1997 | Heard |
| 5,458,598 A | 10/1995 | Feinberg et al. | D384,413 S | 9/1997 | Zlock et al. |
| 5,460,629 A | 10/1995 | Shlain et al. | 5,662,667 A | 9/1997 | Knodel |
| 5,461,765 A | 10/1995 | Linden et al. | 5,665,100 A | 9/1997 | Yoon |
| 5,462,546 A | 10/1995 | Rydell | 5,667,526 A | 9/1997 | Levin |
| 5,472,442 A | 12/1995 | Klicek | 5,674,220 A | 10/1997 | Fox et al. |
| 5,472,443 A | 12/1995 | Cordis et al. | 5,674,229 A | 10/1997 | Tovey et al. |
| 5,478,351 A | 12/1995 | Meade et al. | 5,681,282 A | 10/1997 | Eggers et al. |
| 5,480,406 A | 1/1996 | Nolan et al. | 5,688,270 A | 11/1997 | Yates et al. |
| 5,480,409 A | 1/1996 | Riza | 5,690,652 A | 11/1997 | Wurster et al. |
| 5,484,436 A | 1/1996 | Eggers et al. | 5,690,653 A | 11/1997 | Richardson et al. |
| 5,493,899 A | 2/1996 | Beck et al. | 5,693,051 A | 12/1997 | Schulze et al. |
| 5,496,312 A | 3/1996 | Klicek | 5,693,920 A | 12/1997 | Maeda |
| 5,496,317 A | 3/1996 | Goble et al. | 5,695,522 A | 12/1997 | LeMaire, III et al. |
| 5,496,347 A | 3/1996 | Hashiguchi et al. | 5,700,261 A | 12/1997 | Brinkerhoff |
| 5,499,997 A | 3/1996 | Sharpe et al. | 5,700,270 A | 12/1997 | Peyser et al. |
| 5,509,922 A | 4/1996 | Aranyi et al. | 5,702,390 A | 12/1997 | Austin et al. |
| 5,512,721 A | 4/1996 | Young et al. | 5,707,369 A | 1/1998 | Vaitekunas et al. |
| 5,514,134 A | 5/1996 | Rydell et al. | 5,709,680 A | 1/1998 | Yates et al. |
| 5,520,702 A | 5/1996 | Sauer et al. | 5,716,366 A | 2/1998 | Yates |
| 5,527,313 A | 6/1996 | Scott et al. | 5,720,744 A | 2/1998 | Eggleston et al. |
| 5,528,833 A | 6/1996 | Sakuma | 5,722,421 A | 3/1998 | Francese et al. |
| 5,529,067 A | 6/1996 | Larsen et al. | 5,725,536 A | 3/1998 | Oberlin et al. |
| 5,531,744 A | 7/1996 | Nardella et al. | 5,727,428 A | 3/1998 | LeMaire, III et al. |
| 5,536,251 A | 7/1996 | Evard et al. | 5,735,848 A | 4/1998 | Yates et al. |
| 5,540,684 A | 7/1996 | Hassler, Jr. | 5,743,906 A | 4/1998 | Parins et al. |
| 5,540,685 A | 7/1996 | Parins et al. | 5,752,973 A | 5/1998 | Kieturakis |
| 5,540,706 A | 7/1996 | Aust et al. | 5,755,717 A | 5/1998 | Yates et al. |
| 5,540,715 A | 7/1996 | Katsaros et al. | 5,759,188 A | 6/1998 | Yoon |
| 5,542,945 A | 8/1996 | Fritzsch | 5,762,255 A | 6/1998 | Chrisman et al. |

| | | |
|---|---|---|
| 5,762,609 A | 6/1998 | Benaron et al. |
| 5,766,130 A | 6/1998 | Selmonosky |
| 5,766,166 A | 6/1998 | Hooven |
| 5,766,170 A | 6/1998 | Eggers |
| 5,766,196 A | 6/1998 | Griffiths |
| 5,769,849 A | 6/1998 | Eggers |
| 5,772,655 A | 6/1998 | Bauer et al. |
| 5,772,670 A | 6/1998 | Brosa |
| 5,776,128 A | 7/1998 | Eggers |
| 5,776,130 A | 7/1998 | Buysse et al. |
| 5,776,156 A | 7/1998 | Shikhman |
| 5,779,646 A | 7/1998 | Koblish et al. |
| 5,779,701 A | 7/1998 | McBrayer et al. |
| 5,779,727 A | 7/1998 | Orejola |
| H1745 H | 8/1998 | Paraschac |
| 5,792,137 A | 8/1998 | Carr et al. |
| 5,792,165 A | 8/1998 | Klieman et al. |
| 5,792,177 A | 8/1998 | Kaseda |
| 5,797,537 A | 8/1998 | Oberlin et al. |
| 5,797,927 A | 8/1998 | Yoon |
| 5,797,938 A | 8/1998 | Paraschac et al. |
| 5,797,941 A | 8/1998 | Schulze et al. |
| 5,797,958 A | 8/1998 | Yoon |
| 5,800,449 A | 9/1998 | Wales |
| 5,807,393 A | 9/1998 | Williamson, IV et al. |
| 5,810,764 A | 9/1998 | Eggers et al. |
| 5,810,805 A | 9/1998 | Sutcu et al. |
| 5,810,808 A | 9/1998 | Eggers |
| 5,810,811 A | 9/1998 | Yates et al. |
| 5,810,877 A | 9/1998 | Roth et al. |
| 5,814,043 A | 9/1998 | Shapeton |
| 5,814,054 A | 9/1998 | Kortenbach et al. |
| 5,817,093 A | 10/1998 | Williamson, IV et al. |
| 5,817,119 A | 10/1998 | Klieman et al. |
| 5,820,630 A | 10/1998 | Lind |
| 5,824,978 A | 10/1998 | Karasik et al. |
| 5,827,271 A | 10/1998 | Buysse et al. |
| 5,827,279 A | 10/1998 | Hughett et al. |
| 5,827,281 A | 10/1998 | Levin |
| 5,827,323 A | 10/1998 | Klieman et al. |
| 5,827,548 A | 10/1998 | Lavallee et al. |
| 5,830,212 A | 11/1998 | Cartmell et al. |
| 5,833,690 A | 11/1998 | Yates et al. |
| D402,028 S | 12/1998 | Grimm et al. |
| 5,843,080 A | 12/1998 | Fleenor et al. |
| 5,849,022 A | 12/1998 | Sakashita et al. |
| 5,851,214 A | 12/1998 | Larsen et al. |
| 5,853,412 A | 12/1998 | Mayenberger |
| 5,859,527 A | 1/1999 | Cook |
| 5,860,976 A | 1/1999 | Billings et al. |
| 5,865,361 A | 2/1999 | Milliman et al. |
| 5,876,401 A | 3/1999 | Schulze et al. |
| 5,876,412 A | 3/1999 | Piraka |
| 5,882,567 A | 3/1999 | Cavallaro et al. |
| 5,891,141 A | 4/1999 | Rydell |
| 5,891,142 A | 4/1999 | Eggers et al. |
| 5,893,863 A | 4/1999 | Yoon |
| 5,893,875 A | 4/1999 | O'Connor et al. |
| 5,893,877 A | 4/1999 | Gampp, Jr. et al. |
| 5,897,563 A | 4/1999 | Yoon et al. |
| 5,902,301 A | 5/1999 | Olig |
| 5,906,630 A | 5/1999 | Anderhub et al. |
| 5,908,420 A | 6/1999 | Parins et al. |
| 5,908,432 A | 6/1999 | Pan |
| 5,911,719 A | 6/1999 | Eggers |
| 5,913,874 A | 6/1999 | Berns et al. |
| 5,921,916 A | 7/1999 | Aeikens et al. |
| 5,921,984 A | 7/1999 | Sutcu et al. |
| 5,925,043 A | 7/1999 | Kumar et al. |
| 5,928,136 A | 7/1999 | Barry |
| 5,935,126 A | 8/1999 | Riza |
| 5,938,589 A | 8/1999 | Wako et al. |
| 5,941,869 A | 8/1999 | Patterson et al. |
| 5,944,718 A | 8/1999 | Dafforn et al. |
| 5,951,545 A | 9/1999 | Schilling et al. |
| 5,951,546 A | 9/1999 | Lorentzen |
| 5,951,549 A | 9/1999 | Richardson et al. |
| 5,954,720 A | 9/1999 | Wilson et al. |
| 5,954,731 A | 9/1999 | Yoon |
| 5,954,733 A | 9/1999 | Yoon |
| 5,957,923 A | 9/1999 | Hahnen et al. |
| 5,957,937 A | 9/1999 | Yoon |
| 5,960,544 A | 10/1999 | Beyers |
| 5,961,514 A | 10/1999 | Long et al. |
| 5,964,758 A | 10/1999 | Dresden |
| D416,089 S | 11/1999 | Barton et al. |
| 5,976,132 A | 11/1999 | Morris |
| 5,984,932 A | 11/1999 | Yoon |
| 5,984,938 A | 11/1999 | Yoon |
| 5,984,939 A | 11/1999 | Yoon |
| 5,989,277 A | 11/1999 | LeMaire, III et al. |
| 5,993,466 A | 11/1999 | Yoon |
| 5,993,467 A | 11/1999 | Yoon |
| 5,997,565 A | 12/1999 | Inoue |
| 6,004,332 A | 12/1999 | Yoon et al. |
| 6,004,335 A | 12/1999 | Vaitekunas et al. |
| 6,010,516 A | 1/2000 | Hulka et al. |
| 6,017,354 A | 1/2000 | Culp et al. |
| 6,017,358 A | 1/2000 | Yoon et al. |
| 6,021,693 A | 2/2000 | Feng-Sing |
| 6,024,741 A | 2/2000 | Williamson et al. |
| 6,024,743 A | 2/2000 | Edwards |
| 6,024,744 A | 2/2000 | Kese et al. |
| 6,027,522 A | 2/2000 | Palmer |
| 6,030,384 A | 2/2000 | Nezhat |
| 6,033,399 A | 3/2000 | Gines |
| 6,039,733 A | 3/2000 | Buysse et al. |
| 6,041,679 A | 3/2000 | Slater et al. |
| 6,050,996 A | 4/2000 | Schmaltz et al. |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| 6,059,782 A | 5/2000 | Novak et al. |
| 6,066,139 A | 5/2000 | Ryan et al. |
| 6,071,283 A | 6/2000 | Nardella et al. |
| 6,074,386 A | 6/2000 | Goble et al. |
| 6,077,287 A | 6/2000 | Taylor et al. |
| 6,080,180 A | 6/2000 | Yoon et al. |
| RE36,795 E | 7/2000 | Rydell |
| 6,083,223 A | 7/2000 | Baker |
| 6,086,586 A | 7/2000 | Hooven |
| 6,086,601 A | 7/2000 | Yoon |
| 6,090,107 A | 7/2000 | Borgmeier et al. |
| 6,090,123 A | 7/2000 | Culp et al. |
| 6,096,037 A | 8/2000 | Mulier et al. |
| 6,099,550 A | 8/2000 | Yoon |
| 6,102,909 A | 8/2000 | Chen et al. |
| 6,106,542 A | 8/2000 | Toybin et al. |
| 6,110,171 A | 8/2000 | Rydell |
| 6,113,596 A | 9/2000 | Hooven et al. |
| 6,113,598 A | 9/2000 | Baker |
| 6,117,158 A | 9/2000 | Measamer et al. |
| 6,122,549 A | 9/2000 | Sharkey et al. |
| 6,123,701 A | 9/2000 | Nezhat |
| H1904 H | 10/2000 | Yates et al. |
| 6,126,658 A | 10/2000 | Baker |
| 6,126,665 A | 10/2000 | Yoon |
| 6,139,563 A | 10/2000 | Cosgrove, III et al. |
| 6,143,005 A | 11/2000 | Yoon et al. |
| 6,152,923 A | 11/2000 | Ryan |
| 6,162,220 A | 12/2000 | Nezhat |
| 6,171,316 B1 | 1/2001 | Kovac et al. |
| 6,174,309 B1 | 1/2001 | Wrublewski et al. |
| 6,174,310 B1 | 1/2001 | Kirwan, Jr. |
| 6,178,628 B1 | 1/2001 | Clemens et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,190,400 B1 | 2/2001 | Vandemoer et al. |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,206,893 B1 | 3/2001 | Klein et al. |
| 6,214,028 B1 | 4/2001 | Yoon et al. |
| 6,217,602 B1 | 4/2001 | Redmon |

| | | |
|---|---|---|
| 6,217,615 B1 | 4/2001 | Sioshansi et al. |
| 6,221,039 B1 | 4/2001 | Durgin et al. |
| 6,223,100 B1 | 4/2001 | Green |
| 6,224,593 B1 | 5/2001 | Ryan et al. |
| 6,224,614 B1 | 5/2001 | Yoon |
| 6,228,080 B1 | 5/2001 | Gines |
| 6,228,083 B1 | 5/2001 | Lands et al. |
| 6,248,124 B1 | 6/2001 | Pedros et al. |
| 6,248,944 B1 | 6/2001 | Ito |
| 6,261,307 B1 | 7/2001 | Yoon et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,298,550 B1 | 10/2001 | Kirwan |
| 6,302,424 B1 | 10/2001 | Gisinger et al. |
| 6,303,166 B1 | 10/2001 | Kolbe et al. |
| 6,309,404 B1 | 10/2001 | Krzyzanowski |
| 6,319,262 B1 | 11/2001 | Bates et al. |
| 6,319,451 B1 | 11/2001 | Brune |
| 6,322,561 B1 | 11/2001 | Eggers et al. |
| 6,322,580 B1 | 11/2001 | Kanner |
| 6,325,795 B1 | 12/2001 | Lindemann et al. |
| 6,329,778 B1 | 12/2001 | Culp et al. |
| 6,334,860 B1 | 1/2002 | Dorn |
| 6,334,861 B1 | 1/2002 | Chandler et al. |
| 6,345,532 B1 | 2/2002 | Coudray et al. |
| 6,350,264 B1 | 2/2002 | Hooven |
| D454,951 S | 3/2002 | Bon |
| 6,352,536 B1 | 3/2002 | Buysse et al. |
| 6,358,249 B1 | 3/2002 | Chen et al. |
| 6,358,259 B1 | 3/2002 | Swain et al. |
| 6,358,268 B1 | 3/2002 | Hunt et al. |
| 6,361,534 B1 | 3/2002 | Chen et al. |
| 6,364,879 B1 | 4/2002 | Chen et al. |
| D457,958 S | 5/2002 | Dycus et al. |
| D457,959 S | 5/2002 | Tetzlaff et al. |
| 6,387,094 B1 | 5/2002 | Eitenmuller |
| 6,391,035 B1 | 5/2002 | Appleby et al. |
| 702,472 A1 | 6/2002 | Pignolet |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,432,112 B2 | 8/2002 | Brock et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,129 B2 | 10/2002 | Scarfi |
| 6,458,130 B1 | 10/2002 | Frazier et al. |
| 6,461,352 B2 | 10/2002 | Morgan et al. |
| 6,461,368 B2 | 10/2002 | Fogarty et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,471,696 B1 | 10/2002 | Berube et al. |
| D465,281 S | 11/2002 | Lang |
| D466,209 S | 11/2002 | Bon |
| 6,485,489 B2 | 11/2002 | Teirstein et al. |
| 6,494,888 B1 | 12/2002 | Laufer et al. |
| 6,500,176 B1 | 12/2002 | Truckai et al. |
| 6,506,196 B1 | 1/2003 | Laufer |
| 6,508,815 B1 | 1/2003 | Strul et al. |
| 6,511,480 B1 | 1/2003 | Tetzlaff et al. |
| 6,514,215 B1 | 2/2003 | Ouchi |
| 6,514,252 B2 | 2/2003 | Nezhat et al. |
| 6,517,539 B1 | 2/2003 | Smith et al. |
| 6,527,771 B1 | 3/2003 | Weadock et al. |
| 6,533,784 B2 | 3/2003 | Truckai et al. |
| 6,545,239 B2 | 4/2003 | Spedale et al. |
| 728,883 A1 | 5/2003 | Downes |
| 6,558,385 B1 | 5/2003 | McClurken et al. |
| 6,562,037 B2 | 5/2003 | Paton et al. |
| 6,569,105 B1 | 5/2003 | Kortenbach et al. |
| 6,582,450 B2 | 6/2003 | Ouchi |
| 6,585,735 B1 | 7/2003 | Frazier et al. |
| 6,602,252 B2 | 8/2003 | Mollenauer |
| 6,605,790 B2 | 8/2003 | Yoshida |
| 6,616,654 B2 | 9/2003 | Mollenauer |
| 6,616,658 B2 | 9/2003 | Ineson |
| 6,616,661 B2 | 9/2003 | Wellman et al. |
| 6,620,161 B2 | 9/2003 | Schulze et al. |
| 6,620,184 B2 | 9/2003 | De Laforcade et al. |
| 6,626,901 B1 | 9/2003 | Treat et al. |
| 6,638,287 B2 | 10/2003 | Danitz et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,175 B2 | 12/2003 | Francischelli et al. |
| 6,656,177 B2 | 12/2003 | Truckai et al. |
| 6,660,072 B2 | 12/2003 | Chatterjee |
| 6,663,639 B1 | 12/2003 | Laufer et al. |
| 6,663,641 B1 | 12/2003 | Kovac et al. |
| 6,666,854 B1 | 12/2003 | Lange |
| 6,669,696 B2 | 12/2003 | Bacher et al. |
| 6,673,092 B1 | 1/2004 | Bacher |
| 6,676,660 B2 | 1/2004 | Wampler et al. |
| 6,676,676 B2 | 1/2004 | Danitz et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,693,246 B1 | 2/2004 | Rudolph et al. |
| 6,695,840 B2 | 2/2004 | Schulze |
| 6,702,810 B2 | 3/2004 | McClurken et al. |
| 6,723,092 B2 | 4/2004 | Brown et al. |
| 6,726,068 B2 | 4/2004 | Miller |
| 6,726,686 B2 | 4/2004 | Buysse et al. |
| 6,726,694 B2 | 4/2004 | Blatter et al. |
| 6,733,498 B2 | 5/2004 | Paton et al. |
| 6,733,501 B2 | 5/2004 | Levine |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,743,239 B1 | 6/2004 | Kuehn et al. |
| 6,743,240 B2 | 6/2004 | Smith et al. |
| 6,755,843 B2 | 6/2004 | Chung et al. |
| 6,756,553 B1 | 6/2004 | Yamaguchi et al. |
| 6,757,977 B2 | 7/2004 | Dambal et al. |
| 6,758,846 B2 | 7/2004 | Goble et al. |
| D493,888 S | 8/2004 | Reschke |
| 6,770,072 B2 | 8/2004 | Truckai et al. |
| 6,773,409 B2 | 8/2004 | Truckai et al. |
| 6,773,432 B1 | 8/2004 | Clayman et al. |
| 6,773,434 B2 | 8/2004 | Ciarrocca |
| 6,773,441 B1 | 8/2004 | Laufer et al. |
| 6,775,575 B2 | 8/2004 | Bommannan et al. |
| 6,776,780 B2 | 8/2004 | Mulier et al. |
| 6,786,905 B2 | 9/2004 | Swanson et al. |
| 6,790,217 B2 | 9/2004 | Schulze et al. |
| 6,796,981 B2 | 9/2004 | Wham et al. |
| D496,997 S | 10/2004 | Dycus et al. |
| 6,800,825 B1 | 10/2004 | Sasaki et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,818,007 B1 | 11/2004 | Dampney et al. |
| 6,821,285 B2 | 11/2004 | Laufer et al. |
| 6,830,174 B2 | 12/2004 | Hillstead et al. |
| 6,835,200 B2 | 12/2004 | Laufer et al. |
| 6,857,357 B2 | 2/2005 | Fujii |
| D502,994 S | 3/2005 | Blake, III |
| 6,860,880 B2 | 3/2005 | Treat et al. |
| 6,887,240 B1 | 5/2005 | Lands et al. |
| 6,889,116 B2 | 5/2005 | Jinno |
| 6,908,463 B2 | 6/2005 | Treat et al. |

| | | | |
|---|---|---|---|
| 6,914,201 B2 | 7/2005 | Van Vooren et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| D509,297 S | 9/2005 | Wells |
| 6,942,662 B2 | 9/2005 | Goble et al. |
| 6,943,311 B2 | 9/2005 | Miyako |
| 6,951,559 B1 | 10/2005 | Greep |
| 6,953,430 B2 | 10/2005 | Kidooka |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,972,017 B2 | 12/2005 | Smith et al. |
| 6,976,492 B2 | 12/2005 | Ingle et al. |
| 6,977,495 B2 | 12/2005 | Donofrio |
| 6,979,786 B2 | 12/2005 | Aukland et al. |
| 6,981,628 B2 | 1/2006 | Wales |
| 6,987,244 B2 | 1/2006 | Bauer |
| 6,994,707 B2 | 2/2006 | Ellman et al. |
| 6,994,709 B2 | 2/2006 | Iida |
| 6,997,931 B2 | 2/2006 | Sauer et al. |
| 7,001,381 B2 | 2/2006 | Harano et al. |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,489 B2 | 5/2006 | Griego et al. |
| 7,052,496 B2 | 5/2006 | Yamauchi |
| 7,063,715 B2 | 6/2006 | Onuki et al. |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,083,620 B2 | 8/2006 | Jahns et al. |
| 7,087,051 B2 | 8/2006 | Bourne et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,107,124 B2 | 9/2006 | Green |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| 7,137,980 B2 | 11/2006 | Buysse et al. |
| D533,274 S | 12/2006 | Visconti et al. |
| D533,942 S | 12/2006 | Kerr et al. |
| 7,145,757 B2 | 12/2006 | Shea et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| 7,153,314 B2 | 12/2006 | Laufer et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |
| 7,166,106 B2 | 1/2007 | Bartel et al. |
| 7,169,145 B2 | 1/2007 | Isaacson et al. |
| 7,169,146 B2 | 1/2007 | Truckai et al. |
| 7,179,255 B2 | 2/2007 | Lettice et al. |
| 7,179,258 B2 | 2/2007 | Buysse et al. |
| D538,932 S | 3/2007 | Malik |
| 7,195,631 B2 | 3/2007 | Dumbauld |
| D541,418 S | 4/2007 | Schechter et al. |
| 7,207,990 B2 | 4/2007 | Lands et al. |
| D541,611 S | 5/2007 | Aglassinger |
| D541,938 S | 5/2007 | Kerr et al. |
| 7,223,264 B2 | 5/2007 | Daniel et al. |
| 7,223,265 B2 | 5/2007 | Keppel |
| D545,432 S | 6/2007 | Watanabe |
| 7,232,440 B2 | 6/2007 | Dumbauld et al. |
| D547,154 S | 7/2007 | Lee |
| 7,238,184 B2 | 7/2007 | Megerman et al. |
| 7,241,288 B2 | 7/2007 | Braun |
| 7,241,296 B2 | 7/2007 | Buysse et al. |
| 7,244,257 B2 | 7/2007 | Podjahsky et al. |
| 7,246,734 B2 | 7/2007 | Shelton, IV |
| 7,248,944 B2 | 7/2007 | Green |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,300,435 B2 | 11/2007 | Wham et al. |
| 7,303,557 B2 | 12/2007 | Wham et al. |
| 7,311,709 B2 | 12/2007 | Truckai et al. |
| 7,314,471 B2 | 1/2008 | Holman |
| 7,318,823 B2 | 1/2008 | Sharps et al. |
| 7,329,256 B2 | 2/2008 | Johnson et al. |
| 7,329,257 B2 | 2/2008 | Kanehira et al. |
| D564,662 S | 3/2008 | Moses et al. |
| 7,338,526 B2 | 3/2008 | Steinberg |
| 7,342,754 B2 | 3/2008 | Fitzgerald et al. |
| 7,344,268 B2 | 3/2008 | Jhigamian |
| D567,943 S | 4/2008 | Moses et al. |
| 7,354,440 B2 | 4/2008 | Truckai et al. |
| 7,367,976 B2 | 5/2008 | Lawes et al. |
| 7,377,920 B2 | 5/2008 | Buysse et al. |
| 7,384,420 B2 | 6/2008 | Dycus et al. |
| 7,384,421 B2 | 6/2008 | Hushka |
| 7,396,265 B2 | 7/2008 | Darley et al. |
| 7,396,336 B2 | 7/2008 | Orszulak et al. |
| 7,396,356 B2 | 7/2008 | Mollenauer |
| D575,395 S | 8/2008 | Hushka |
| D575,401 S | 8/2008 | Hixson et al. |
| 7,425,835 B2 | 9/2008 | Eisele |
| 7,431,721 B2 | 10/2008 | Paton et al. |
| 7,435,249 B2 | 10/2008 | Buysse et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| D582,038 S | 12/2008 | Swoyer et al. |
| 7,458,972 B2 | 12/2008 | Keppel |
| 7,473,253 B2 | 1/2009 | Dycus et al. |
| 7,481,810 B2 | 1/2009 | Dumbauld et al. |
| 7,487,780 B2 | 2/2009 | Hooven |
| 7,491,201 B2 | 2/2009 | Shields et al. |
| 7,491,202 B2 | 2/2009 | Odom et al. |
| 7,500,975 B2 | 3/2009 | Cunningham et al. |
| 7,503,474 B2 | 3/2009 | Hillstead et al. |
| 7,510,556 B2 | 3/2009 | Nguyen et al. |
| 7,513,898 B2 | 4/2009 | Johnson et al. |
| 7,517,351 B2 | 4/2009 | Culp et al. |
| 7,540,872 B2 | 6/2009 | Schechter et al. |
| 7,549,995 B2 | 6/2009 | Schultz |
| 7,553,312 B2 | 6/2009 | Tetzlaff et al. |
| 7,582,087 B2 | 9/2009 | Tetzlaff et al. |
| 7,588,565 B2 | 9/2009 | Marchitto et al. |
| 7,594,916 B2 | 9/2009 | Weinberg |
| 7,597,693 B2 | 10/2009 | Garrison |
| 7,621,910 B2 | 11/2009 | Sugi |
| 7,628,791 B2 | 12/2009 | Garrison et al. |
| 7,628,792 B2 | 12/2009 | Guerra |
| 7,637,409 B2 | 12/2009 | Marczyk |
| 7,641,653 B2 | 1/2010 | Dalla Betta et al. |
| 7,651,493 B2 | 1/2010 | Arts et al. |
| 7,651,494 B2 | 1/2010 | McClurken et al. |
| 7,655,007 B2 | 2/2010 | Baily |
| 7,668,597 B2 | 2/2010 | Engmark et al. |
| 7,678,111 B2 | 3/2010 | Mulier et al. |
| 7,686,804 B2 | 3/2010 | Johnson et al. |
| 7,686,827 B2 | 3/2010 | Hushka |

| | | |
|---|---|---|
| 7,708,735 B2 | 5/2010 | Chapman et al. |
| 7,717,115 B2 | 5/2010 | Barrett et al. |
| 7,717,904 B2 | 5/2010 | Suzuki et al. |
| 7,722,607 B2 | 5/2010 | Dumbauld et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| 7,731,717 B2 | 6/2010 | Odom et al. |
| 7,744,615 B2 | 6/2010 | Couture |
| 7,749,217 B2 | 7/2010 | Podhajsky |
| 7,753,908 B2 | 7/2010 | Swanson |
| 7,753,909 B2 | 7/2010 | Chapman et al. |
| D621,503 S | 8/2010 | Otten et al. |
| 7,766,910 B2 | 8/2010 | Hixson et al. |
| 7,771,425 B2 | 8/2010 | Dycus et al. |
| 7,776,036 B2 | 8/2010 | Schechter et al. |
| 7,776,037 B2 | 8/2010 | Odom |
| 7,780,662 B2 | 8/2010 | Bahney |
| 7,789,878 B2 | 9/2010 | Dumbauld et al. |
| 7,799,026 B2 | 9/2010 | Schechter et al. |
| 7,799,028 B2 | 9/2010 | Schechter et al. |
| 7,811,283 B2 | 10/2010 | Moses et al. |
| 2002/0107517 A1 | 8/2002 | Witt et al. |
| 2002/0111624 A1 | 8/2002 | Witt et al. |
| 2003/0014052 A1 | 1/2003 | Buysse et al. |
| 2003/0014053 A1 | 1/2003 | Nguyen et al. |
| 2003/0018332 A1 | 1/2003 | Schmaltz et al. |
| 2003/0069570 A1 | 4/2003 | Witzel et al. |
| 2003/0109875 A1 | 6/2003 | Tetzlaff et al. |
| 2003/0114851 A1 | 6/2003 | Truckai et al. |
| 2003/0130653 A1 | 7/2003 | Sixto, Jr. et al. |
| 2003/0139741 A1 | 7/2003 | Goble et al. |
| 2003/0158548 A1 | 8/2003 | Phan et al. |
| 2003/0171747 A1 | 9/2003 | Kanehira et al. |
| 2003/0181910 A1 | 9/2003 | Dycus et al. |
| 2003/0216732 A1 | 11/2003 | Truckai et al. |
| 2003/0229344 A1 | 12/2003 | Dycus et al. |
| 2003/0236325 A1 | 12/2003 | Bonora |
| 2004/0030330 A1 | 2/2004 | Brassell et al. |
| 2004/0064151 A1 | 4/2004 | Mollenauer |
| 2004/0073238 A1 | 4/2004 | Makower |
| 2004/0073256 A1 | 4/2004 | Marchitto et al. |
| 2004/0115296 A1 | 6/2004 | Duffin |
| 2004/0199181 A1 | 10/2004 | Knodel et al. |
| 2004/0210282 A1 | 10/2004 | Flock et al. |
| 2004/0224590 A1 | 11/2004 | Rawa et al. |
| 2004/0236326 A1 | 11/2004 | Schulze et al. |
| 2004/0249374 A1 | 12/2004 | Tetzlaff et al. |
| 2004/0260281 A1 | 12/2004 | Baxter, III et al. |
| 2005/0004564 A1 | 1/2005 | Wham et al. |
| 2005/0004569 A1 | 1/2005 | Witt et al. |
| 2005/0033278 A1 | 2/2005 | McClurken et al. |
| 2005/0059858 A1 | 3/2005 | Frith et al. |
| 2005/0059934 A1 | 3/2005 | Wenchell et al. |
| 2005/0096645 A1 | 5/2005 | Wellman et al. |
| 2005/0101952 A1 | 5/2005 | Lands et al. |
| 2005/0149017 A1 | 7/2005 | Dycus |
| 2005/0197659 A1 | 9/2005 | Bahney |
| 2005/0203504 A1 | 9/2005 | Wham et al. |
| 2005/0283148 A1 | 12/2005 | Janssen et al. |
| 2006/0052779 A1 | 3/2006 | Hammill |
| 2006/0064086 A1 | 3/2006 | Odom |
| 2006/0079891 A1 | 4/2006 | Arts et al. |
| 2006/0079933 A1 | 4/2006 | Hushka et al. |
| 2006/0084973 A1 | 4/2006 | Hushka |
| 2006/0116675 A1 | 6/2006 | McClurken et al. |
| 2006/0167452 A1 | 7/2006 | Moses et al. |
| 2006/0173452 A1 | 8/2006 | Buysse et al. |
| 2006/0190035 A1 | 8/2006 | Hushka et al. |
| 2006/0217709 A1 | 9/2006 | Couture et al. |
| 2006/0253126 A1 | 11/2006 | Bjerken et al. |
| 2006/0259036 A1 | 11/2006 | Tetzlaff et al. |
| 2006/0264922 A1 | 11/2006 | Sartor et al. |
| 2006/0283093 A1 | 12/2006 | Petrovic et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0043353 A1 | 2/2007 | Dycus et al. |
| 2007/0060919 A1 | 3/2007 | Isaacson et al. |
| 2007/0062017 A1 | 3/2007 | Dycus et al. |
| 2007/0074807 A1 | 4/2007 | Guerra |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0173804 A1 | 7/2007 | Wham et al. |
| 2007/0173811 A1 | 7/2007 | Couture et al. |
| 2007/0173813 A1 | 7/2007 | Odom |
| 2007/0198011 A1 | 8/2007 | Sugita |
| 2007/0213712 A1 | 9/2007 | Buysse et al. |
| 2007/0255279 A1 | 11/2007 | Buysse et al. |
| 2007/0260235 A1 | 11/2007 | Podhajsky |
| 2007/0260238 A1 | 11/2007 | Guerra |
| 2007/0260242 A1 | 11/2007 | Dycus et al. |
| 2007/0265616 A1 | 11/2007 | Couture et al. |
| 2008/0004616 A1 | 1/2008 | Patrick |
| 2008/0015575 A1 | 1/2008 | Odom et al. |
| 2008/0033428 A1 | 2/2008 | Artale et al. |
| 2008/0039831 A1 | 2/2008 | Odom et al. |
| 2008/0039835 A1 | 2/2008 | Johnson et al. |
| 2008/0045947 A1 | 2/2008 | Johnson et al. |
| 2008/0058802 A1 | 3/2008 | Couture et al. |
| 2008/0082100 A1 | 4/2008 | Orton et al. |
| 2008/0091189 A1 | 4/2008 | Carlton |
| 2008/0125767 A1 | 5/2008 | Blaha |
| 2008/0125797 A1 | 5/2008 | Kelleher |
| 2008/0195093 A1 | 8/2008 | Couture et al. |
| 2008/0208289 A1 | 8/2008 | Darley et al. |
| 2008/0215050 A1 | 9/2008 | Bakos |
| 2008/0215051 A1 | 9/2008 | Buysse et al. |
| 2008/0234701 A1 | 9/2008 | Morales et al. |
| 2008/0243120 A1 | 10/2008 | Lawes et al. |
| 2008/0249527 A1 | 10/2008 | Couture |
| 2008/0294222 A1 | 11/2008 | Schechter |
| 2008/0296347 A1 | 12/2008 | Shelton, IV et al. |
| 2008/0300613 A1 | 12/2008 | Shelton, IV et al. |
| 2008/0312653 A1 | 12/2008 | Arts et al. |
| 2008/0319442 A1 | 12/2008 | Unger et al. |
| 2009/0012520 A1 | 1/2009 | Hixson et al. |
| 2009/0015832 A1 | 1/2009 | Popovic et al. |
| 2009/0024126 A1 | 1/2009 | Artale et al. |
| 2009/0036881 A1 | 2/2009 | Artale et al. |
| 2009/0036899 A1 | 2/2009 | Carlton et al. |
| 2009/0043304 A1 | 2/2009 | Tetzlaff et al. |
| 2009/0048596 A1 | 2/2009 | Shields et al. |
| 2009/0062794 A1 | 3/2009 | Buysse et al. |
| 2009/0065565 A1 | 3/2009 | Cao |
| 2009/0076534 A1 | 3/2009 | Shelton, IV et al. |
| 2009/0082766 A1 | 3/2009 | Unger et al. |
| 2009/0082767 A1 | 3/2009 | Unger et al. |
| 2009/0082769 A1 | 3/2009 | Unger et al. |
| 2009/0088738 A1 | 4/2009 | Guerra et al. |
| 2009/0088739 A1 | 4/2009 | Hushka et al. |
| 2009/0088740 A1 | 4/2009 | Guerra et al. |
| 2009/0088741 A1 | 4/2009 | Hushka et al. |
| 2009/0088744 A1 | 4/2009 | Townsend |
| 2009/0088745 A1 | 4/2009 | Hushka et al. |
| 2009/0088746 A1 | 4/2009 | Hushka et al. |
| 2009/0088747 A1 | 4/2009 | Hushka et al. |
| 2009/0088748 A1 | 4/2009 | Guerra et al. |
| 2009/0088749 A1 | 4/2009 | Hushka et al. |
| 2009/0088750 A1 | 4/2009 | Hushka et al. |
| 2009/0105750 A1 | 4/2009 | Price et al. |
| 2009/0112206 A1 | 4/2009 | Dumbauld et al. |
| 2009/0131934 A1 | 5/2009 | Odom et al. |
| 2009/0149853 A1 | 6/2009 | Shields et al. |
| 2009/0149854 A1 | 6/2009 | Cunningham et al. |
| 2009/0157071 A1 | 6/2009 | Wham et al. |
| 2009/0157072 A1 | 6/2009 | Wham et al. |
| 2009/0157075 A1 | 6/2009 | Wham et al. |
| 2009/0171350 A1 | 7/2009 | Dycus et al. |
| 2009/0171353 A1 | 7/2009 | Johnson et al. |
| 2009/0182327 A1 | 7/2009 | Unger |

| | | | | | | |
|---|---|---|---|---|---|---|
| 2009/0182329 A1 | 7/2009 | Dycus | | EP | 0572131 | 12/1993 |
| 2009/0187188 A1 | 7/2009 | Guerra et al. | | EP | 0584787 | 3/1994 |
| 2009/0198233 A1 | 8/2009 | Chojin | | EP | 0589453 | 3/1994 |
| 2009/0204114 A1 | 8/2009 | Odom | | EP | 0589555 | 3/1994 |
| 2009/0209957 A1 | 8/2009 | Schmaltz et al. | | EP | 0623316 | 11/1994 |
| 2009/0209960 A1 | 8/2009 | Chojin | | EP | 0624348 | 11/1994 |
| 2009/0234354 A1 | 9/2009 | Johnson et al. | | EP | 0650701 | 5/1995 |
| 2009/0248021 A1 | 10/2009 | McKenna | | EP | 0694290 | 3/1996 |
| 2009/0261804 A1 | 10/2009 | McKenna et al. | | EP | 0717966 | 6/1996 |
| 2009/0292282 A9 | 11/2009 | Dycus | | EP | 0754437 | 3/1997 |
| 2009/0306660 A1 | 12/2009 | Johnson et al. | | EP | 0517243 | 9/1997 |
| 2010/0016857 A1 | 1/2010 | McKenna et al. | | EP | 0853922 | 7/1998 |
| 2010/0023009 A1 | 1/2010 | Moses et al. | | EP | 0875209 | 11/1998 |
| 2010/0036375 A1 | 2/2010 | Regadas | | EP | 0878169 | 11/1998 |
| 2010/0042100 A1 | 2/2010 | Tetzlaff et al. | | EP | 0887046 | 1/1999 |
| 2010/0042140 A1 | 2/2010 | Cunningham | | EP | 0923907 | 6/1999 |
| 2010/0042142 A1 | 2/2010 | Cunningham | | EP | 0950378 | 10/1999 |
| 2010/0042143 A1 | 2/2010 | Cunningham | | EP | 0986990 | 3/2000 |
| 2010/0049187 A1 | 2/2010 | Carlton et al. | | EP | 1034747 | 9/2000 |
| 2010/0057081 A1 | 3/2010 | Hanna | | EP | 1034748 | 9/2000 |
| 2010/0057082 A1 | 3/2010 | Hanna | | EP | 1025807 | 10/2000 |
| 2010/0057083 A1 | 3/2010 | Hanna | | EP | 1034746 | 10/2000 |
| 2010/0057084 A1 | 3/2010 | Hanna | | EP | 1050278 | 11/2000 |
| 2010/0063500 A1 | 3/2010 | Muszala | | EP | 1053719 | 11/2000 |
| 2010/0069903 A1 | 3/2010 | Allen, IV et al. | | EP | 1053720 | 11/2000 |
| 2010/0069904 A1 | 3/2010 | Cunningham | | EP | 1055399 | 11/2000 |
| 2010/0069953 A1 | 3/2010 | Cunningham et al. | | EP | 1055400 | 11/2000 |
| 2010/0076427 A1 | 3/2010 | Heard | | EP | 1080694 | 3/2001 |
| 2010/0076430 A1 | 3/2010 | Romero | | EP | 1082944 | 3/2001 |
| 2010/0076431 A1 | 3/2010 | Allen, IV | | EP | 1159926 | 12/2001 |
| 2010/0076432 A1 | 3/2010 | Horner | | EP | 1177771 | 2/2002 |
| 2010/0087816 A1 | 4/2010 | Roy | | EP | 1278007 | 1/2003 |
| 2010/0087818 A1 | 4/2010 | Cunningham | | EP | 1301135 | 4/2003 |
| 2010/0094271 A1 | 4/2010 | Ward et al. | | EP | 1330991 | 7/2003 |
| 2010/0094286 A1 | 4/2010 | Chojin | | EP | 1486177 | 6/2004 |
| 2010/0094287 A1 | 4/2010 | Cunningham et al. | | EP | 1472984 | 11/2004 |
| 2010/0100122 A1 | 4/2010 | Hinton | | EP | 0774232 | 1/2005 |
| 2010/0130971 A1 | 5/2010 | Baily | | EP | 1527747 | 5/2005 |
| 2010/0130977 A1 | 5/2010 | Garrison et al. | | EP | 1530952 | 5/2005 |
| 2010/0145334 A1 | 6/2010 | Olson et al. | | EP | 1532932 | 5/2005 |
| 2010/0145335 A1 | 6/2010 | Johnson et al. | | EP | 1535581 | 6/2005 |
| 2010/0179539 A1 | 7/2010 | Nau, Jr. | | EP | 1609430 | 12/2005 |
| 2010/0179543 A1 | 7/2010 | Johnson et al. | | EP | 1201192 | 2/2006 |
| 2010/0179545 A1 | 7/2010 | Twomey et al. | | EP | 1632192 | 3/2006 |
| 2010/0179546 A1 | 7/2010 | Cunningham | | EP | 1642543 | 4/2006 |
| 2010/0179547 A1 | 7/2010 | Cunningham et al. | | EP | 1645238 | 4/2006 |
| 2010/0204697 A1 | 8/2010 | Dumbauld et al. | | EP | 1645240 | 4/2006 |
| 2010/0204698 A1 | 8/2010 | Chapman et al. | | EP | 1649821 | 4/2006 |
| 2010/0217258 A1 | 8/2010 | Floume et al. | | EP | 1707143 | 10/2006 |
| 2010/0249769 A1 | 9/2010 | Nau, Jr. et al. | | EP | 1767163 | 3/2007 |
| 2010/0249776 A1 | 9/2010 | Kerr | | EP | 1769765 | 4/2007 |
| 2010/0256635 A1 | 10/2010 | McKenna et al. | | EP | 1769766 | 4/2007 |
| | | | | EP | 1785097 | 5/2007 |
| | FOREIGN PATENT DOCUMENTS | | | EP | 1785098 | 5/2007 |
| | | | | EP | 1785101 | 5/2007 |
| CA | 2 520 413 | 3/2007 | | EP | 1810625 | 7/2007 |
| DE | 2415263 | 10/1975 | | EP | 1810628 | 7/2007 |
| DE | 2514501 | 10/1976 | | EP | 1842500 | 10/2007 |
| DE | 2627679 | 1/1977 | | EP | 1878400 | 1/2008 |
| DE | 3423356 | 1/1986 | | EP | 1929970 | 6/2008 |
| DE | 3612646 | 4/1987 | | EP | 1990019 | 11/2008 |
| DE | 8712328 | 3/1988 | | EP | 1683496 | 12/2008 |
| DE | 4303882 | 8/1994 | | EP | 1997438 | 12/2008 |
| DE | 4403252 | 8/1995 | | EP | 1997439 | 12/2008 |
| DE | 19515914 | 7/1996 | | EP | 1527744 | 2/2009 |
| DE | 19506363 | 8/1996 | | EP | 2206474 | 7/2010 |
| DE | 29616210 | 1/1997 | | GB | 623316 | 5/1949 |
| DE | 19608716 | 4/1997 | | GB | 1490585 | 11/1977 |
| DE | 19751106 | 5/1998 | | GB | 2214430 A | 6/1989 |
| DE | 19751108 | 5/1999 | | GB | 2213416 A | 8/1989 |
| DE | 10045375 | 4/2002 | | JP | 61-501068 | 9/1984 |
| DE | 10 2004 026 179 | 12/2005 | | JP | 6-502328 | 3/1992 |
| DE | 20 2007 009317 | 10/2007 | | JP | 5-5106 | 1/1993 |
| DE | 19738457 | 1/2009 | | JP | 5-40112 | 2/1993 |
| EP | 0364216 | 4/1990 | | JP | 06343644 | 12/1994 |
| EP | 0467501 | 1/1992 | | JP | 07265328 | 10/1995 |
| EP | 0509670 | 10/1992 | | JP | 08056955 | 3/1996 |
| EP | 0518230 | 12/1992 | | JP | 08252263 | 10/1996 |
| EP | 0541930 | 5/1993 | | JP | 09010223 | 1/1997 |
| EP | 0306123 | 8/1993 | | | | |

| | | |
|---|---|---|
| JP | 10-24051 | 1/1998 |
| JP | 11-070124 | 5/1998 |
| JP | 2000-102545 | 9/1998 |
| JP | 11-169381 | 6/1999 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 89/00757 | 1/1989 |
| WO | WO 92/04873 | 4/1992 |
| WO | WO 92/06642 | 4/1992 |
| WO | WO 93/19681 | 10/1993 |
| WO | WO 93/21845 | 11/1993 |
| WO | WO 94/08524 | 4/1994 |
| WO | WO 94/20025 | 9/1994 |
| WO | WO 95/02369 | 1/1995 |
| WO | WO 95/07662 | 3/1995 |
| WO | WO 95/15124 | 6/1995 |
| WO | WO 95/20360 | 8/1995 |
| WO | WO 96/05776 | 2/1996 |
| WO | WO 96/11635 | 4/1996 |
| WO | WO 96/22056 | 7/1996 |
| WO | WO 96/13218 | 9/1996 |
| WO | WO 97/00646 | 1/1997 |
| WO | WO 97/00647 | 1/1997 |
| WO | WO 97/10764 | 3/1997 |
| WO | WO 97/18768 | 5/1997 |
| WO | WO 97/24073 | 7/1997 |
| WO | WO 97/24993 | 7/1997 |
| WO | WO 98/14124 | 4/1998 |
| WO | WO 98/27880 | 7/1998 |
| WO | WO 98/31290 | 7/1998 |
| WO | WO 98/43264 | 10/1998 |
| WO | WO 99/03407 | 1/1999 |
| WO | WO 99/03408 | 1/1999 |
| WO | WO 99/03409 | 1/1999 |
| WO | WO 99/03414 | 1/1999 |
| WO | WO 99/12488 | 3/1999 |
| WO | WO 99/23933 | 5/1999 |
| WO | WO 99/40857 | 8/1999 |
| WO | WO 99/40861 | 8/1999 |
| WO | WO 99/51158 | 10/1999 |
| WO | WO 99/66850 | 12/1999 |
| WO | WO 00/24330 | 5/2000 |
| WO | WO 00/24331 | 5/2000 |
| WO | WO 00/33753 | 6/2000 |
| WO | WO 00/36986 | 6/2000 |
| WO | WO 00/41638 | 7/2000 |
| WO | WO 00/47124 | 8/2000 |
| WO | WO 00/53112 | 9/2000 |
| WO | 0100114 A1 | 1/2001 |
| WO | WO 01/01847 | 1/2001 |
| WO | WO 01/17448 | 3/2001 |
| WO | WO 01/54604 | 8/2001 |
| WO | WO 02/07627 | 1/2002 |
| WO | 02/45589 A2 | 6/2002 |
| WO | WO 02/067798 | 9/2002 |
| WO | WO 02/080783 | 10/2002 |
| WO | WO 02/080784 | 10/2002 |
| WO | WO 02/080785 | 10/2002 |
| WO | WO 02/080786 | 10/2002 |
| WO | WO 02/080793 | 10/2002 |
| WO | WO 02/080794 | 10/2002 |
| WO | WO 02/080795 | 10/2002 |
| WO | WO 02/080796 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO 03/061500 | 7/2003 |
| WO | WO 03/090630 | 11/2003 |
| WO | WO 03/101311 | 12/2003 |
| WO | WO 2004/028585 | 4/2004 |
| WO | WO 2004/032776 | 4/2004 |
| WO | WO 2004/032777 | 4/2004 |
| WO | WO 2004/052221 | 6/2004 |
| WO | WO 2004/073488 | 9/2004 |
| WO | WO 2004/073490 | 9/2004 |
| WO | WO 2004/073753 | 9/2004 |
| WO | WO 2004/082495 | 9/2004 |
| WO | WO 2004/098383 | 11/2004 |
| WO | WO 2004/103156 | 12/2004 |
| WO | WO 2005/004734 | 1/2005 |
| WO | WO 2005/004735 | 1/2005 |
| WO | WO 2005/009255 | 2/2005 |
| WO | WO 2005/048809 | 6/2005 |
| WO | WO 2005/050151 | 6/2005 |
| WO | WO 2005/110264 | 11/2005 |
| WO | WO 2008/040483 | 4/2008 |
| WO | WO 2008/045348 | 4/2008 |
| WO | WO 2008/045350 | 4/2008 |
| WO | WO 2008/112147 | 9/2008 |
| WO | WO 2009/005850 | 1/2009 |
| WO | WO 2009/039179 | 3/2009 |
| WO | WO 2009/039510 | 3/2009 |

OTHER PUBLICATIONS

U.S. Appl. No. 09/591,328, filed Jun. 9, 2000.
U.S. Appl. No. 12/336,970, filed Dec. 17, 2008.
U.S. Appl. No. 12/429,533, filed Apr. 24, 2009.
U.S. Appl. No. 12/434,382, filed May 1, 2009.
U.S. Appl. No. 12/437,254, filed May 7, 2009.
U.S. Appl. No. 12/503,256, filed Jul. 15, 2009.
U.S. Appl. No. 12/535,869, filed Aug. 5, 2009.
U.S. Appl. No. 12/543,831, filed Aug. 19, 2009.
U.S. Appl. No. 12/548,031, filed Aug. 26, 2009.
U.S. Appl. No. 12/548,534, filed Aug. 27, 2009.
U.S. Appl. No. 12/548,566, filed Aug. 27, 2009.
U.S. Appl. No. 12/551,944, filed Sep. 1, 2009.
U.S. Appl. No. 12/553,509, filed Sep. 3, 2009.
U.S. Appl. No. 12/556,025, filed Sep. 9, 2009.
U.S. Appl. No. 12/556,407, filed Sep. 9, 2009.
U.S. Appl. No. 12/556,427, filed Sep. 9, 2009.
U.S. Appl. No. 12/556,796, filed Sep. 10, 2009.
U.S. Appl. No. 12/562,281, filed Sep. 18, 2009.
U.S. Appl. No. 12/565,281, filed Sep. 23, 2009.
U.S. Appl. No. 12/568,199, filed Sep. 28, 2009.
U.S. Appl. No. 12/568,282, filed Sep. 28, 2009.
U.S. Appl. No. 12/568,838, filed Sep. 29, 2009.
U.S. Appl. No. 12/569,395, Sep. 29, 2009.
U.S. Appl. No. 12/569,710, filed Sep. 29, 2009.
U.S. Appl. No. 12/574,001, filed Oct. 6, 2009.
U.S. Appl. No. 12/574,292, filed Oct. 6, 2009.
U.S. Appl. No. 12/576,380, filed Oct. 9, 2009.
U.S. Appl. No. 12/597,213, filed Oct. 23, 2009.
U.S. Appl. No. 12/607,191, filed Oct. 28, 2009.
U.S. Appl. No. 12/619,100, filed Nov. 16, 2009.
U.S. Appl. No. 12/692,414, filed Jan. 22, 2010.
U.S. Appl. No. 12/696,592, filed Jan. 29, 2010.
U.S. Appl. No. 12/696,857, filed Jan. 29, 2010.
U.S. Appl. No. 12/700,856, filed Feb. 5, 2010.
U.S. Appl. No. 12/719,407, filed Mar. 8, 2010.
U.S. Appl. No. 12/728,994, filed Mar. 22, 2010.
U.S. Appl. No. 12/748,028, filed Mar. 26, 2010.
U.S. Appl. No. 12/757,340, filed Apr. 9, 2010.
U.S. Appl. No. 12/758,524, filed Apr. 12, 2010.
U.S. Appl. No. 12/758,551, filed Apr. 13, 2010.
U.S. Appl. No. 12/769,444, filed Apr. 28, 2010.
U.S. Appl. No. 12/770,369, filed Apr. 29, 2010.
U.S. Appl. No. 12/770,380, filed Apr. 29, 2010.
U.S. Appl. No. 12/770,387, filed Apr. 29, 2010.
U.S. Appl. No. 12/773,526, filed May 4, 2010.
U.S. Appl. No. 12/773,644, filed May 4, 2010.
U.S. Appl. No. 12/775,553, filed May 7, 2010.
U.S. Appl. No. 12/786,589, filed May 25, 2010.
U.S. Appl. No. 12/791,112, filed Jun. 1, 2010.
U.S. Appl. No. 12/792,001, filed Jun. 2, 2010.
U.S. Appl. No. 12/792,008, filed Jun. 2, 2010.
U.S. Appl. No. 12/792,019, filed Jun. 2, 2010.
U.S. Appl. No. 12/792,038, filed Jun. 2, 2010.

U.S. Appl. No. 12/792,051, filed Jun. 2, 2010.
U.S. Appl. No. 12/792,068, filed Jun. 2, 2010.
U.S. Appl. No. 12/792,097, filed Jun. 2, 2010.
U.S. Appl. No. 12/792,262, filed Jun. 2, 2010.
U.S. Appl. No. 12/792,299, filed Jun. 2, 2010.
U.S. Appl. No. 12/792,330, filed Jun. 2, 2010.
U.S. Appl. No. 12/822,024, filed Jun. 23, 2010.
U.S. Appl. No. 12/821,253, filed Jun. 23, 2010.
U.S. Appl. No. 12/832,772, filed Jul. 8, 2010.
U.S. Appl. No. 12/833,270, filed Jul. 9, 2010.
U.S. Appl. No. 12/843,384, filed Jul. 26, 2010.
U.S. Appl. No. 12/845,203, filed Jul. 28, 2010.
U.S. Appl. No. 12/846,602, filed Jul. 29, 2010.
U.S. Appl. No. 12/853,896, filed Aug. 10, 2010.
U.S. Appl. No. 12/859,896, filed Aug. 20, 2010.
U.S. Appl. No. 12/859,985, filed Aug. 20, 2010.
U.S. Appl. No. 12/861,198, filed Aug. 23, 2010.
U.S. Appl. No. 12/861,209, filed Aug. 23, 2010.
U.S. Appl. No. 12/876,662, filed Sep. 7, 2010.
U.S. Appl. No. 12/876,668, filed Sep. 7, 2010.
U.S. Appl. No. 12/876,680, filed Sep. 7, 2010.
U.S. Appl. No. 12/876,705, filed Sep. 7, 2010.
U.S. Appl. No. 12/876,731, filed Sep. 7, 2010.
U.S. Appl. No. 12/877,199, filed Sep. 8, 2010.
U.S. Appl. No. 12/877,482, filed Sep. 8, 2010.
U.S. Appl. No. 12/879,505, filed Sep. 10, 2010.
U.S. Appl. No. 12/882,304, filed Sep. 15, 2010.
U.S. Appl. No. 12/895,020, filed Sep. 30, 2010.
U.S. Appl. No. 12/896,100, filed Oct. 1, 2010.
U.S. Appl. No. 12/897,346, filed Oct. 4, 2010.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967, British Medical Journal Feb. 6, 1976, (Feb. 6, 1965), vol. 1, nr. 5431 p. 361, ISSN: 0007-1447.
Carbonell et al., "Comparison of the Gyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; Vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.

Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16,2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 157500.9 dated Jul. 30, 2010.
Int'l Search Report EP 10 159205.3 dated Jul. 7, 2010.
Int'l Search Report EP 10 160870.1 dated Aug. 9, 2010.
Int'l Search Report EP 10 161596.1 dated Jul. 28, 2010.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18676 dated Sep. 19, 2003.
Int'l Search Report PCT/US03/28534dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
European Search Report 05004431.2 dated Jun. 28, 2005.

VESSEL SEALING SYSTEM USING CAPACITIVE RF DIELECTRIC HEATING

CROSS-REFERENCE TO RELATED APPLICATIONS

The present application is a divisional of, and claims the benefit of priority to, U.S. patent application No. 11/063,684 filed on Feb. 23, 2005, now U.S. Pat. No. 7,780,662, which claims the benefit of priority to U.S. Provisional Application No. 60/549,232 filed on Mar. 2, 2004, both of which are incorporated herein by reference.

BACKGROUND

1. Technical Field

The present disclosure is directed to electrosurgical systems, and, in particular, to an electrosurgical system for vessel sealing using capacitive radio frequency (RF) dielectric heating.

2. Description of the Related Art

Electrosurgical generators are employed by surgeons in conjunction with an electrosurgical tool to cut, coagulate, desiccate and/or seal patient tissue. High frequency electrical energy, e.g., radio frequency (RF) energy, is produced by the electrosurgical generator and applied to the tissue by the electrosurgical tool. Both monopolar and bipolar configurations are commonly used during electrosurgical procedures.

Electrosurgical generators typically include power supply circuits, front panel interface circuits, and RF output stage circuits. Many electrical designs for electrosurgical generators are known in the field. In certain electrosurgical generator designs, the RF output stage can be adjusted to control the RMS (root mean square) output power. The methods of controlling the RF output stage may include changing the duty cycle, or changing the amplitude of the driving signal to the RF output stage. The method of controlling the RF output stage is described herein as changing an input to the RF output stage.

Electrosurgical techniques have been used to seal or fuse small diameter blood vessels, vascular bundles and tissue. In this application, two layers of tissue are grasped and clamped together while electrosurgical power is applied. By applying a unique combination of pressure, gap distance between opposing seal surfaces and controlling the electrosurgical energy, the two tissue layers are welded or fused together into a single mass with limited demarcation between tissue layers. Tissue fusion is similar to vessel sealing, except that a vessel or duct is not necessarily sealed in this process. For example, tissue fusion may be used instead of staples for surgical anastomosis.

One of the issues associated with electrosurgical sealing or fusion of tissue is undesirable collateral damage to tissue due to the various thermal effects associated with electrosurgically energizing tissue. The tissue at the operative site is heated by electrosurgical current typically applied by the electrosurgical instrument. Healthy tissue adjacent to the operative site may become thermally damaged if too much heat is allowed to build up at the operative site or adjacent the sealing surfaces. For example, during sealing, the heat may conduct or spread to the adjacent tissue and cause a significant region of tissue necrosis. This is known as thermal spread. Thermal spread becomes important when electrosurgical instruments are used in close proximity to delicate anatomical structures. Therefore, an electrosurgical generator that reduces the possibility of thermal spread would offer a better opportunity for a successful surgical outcome.

Another issue associated with electrosurgical tissue sealing or tissue fusion is the buildup of eschar on the surgical instrument. Eschar is a deposit which is created from tissue that is charred by heat. Surgical tools often lose effectiveness when coated with eschar.

In order to effect a proper seal with larger vessels, two predominant mechanical parameters must be accurately controlled—the pressure applied to the vessel and the gap between the electrodes both of which affect thickness of the sealed vessel. More particularly, accurate application of the pressure is important to oppose the walls of the vessel, to reduce the tissue impedance to a low enough value that allows enough electrosurgical energy through the tissue, to overcome the forces of expansion during tissue heating and to contribute to the end tissue thickness which is an indication of a good seal. It has been determined that a fused vessel wall is optimum between about 0.001 and about 0.006 inches. Below this range, the seal may shred or tear and above this range the lumens may not be properly or effectively sealed.

With respect to smaller vessels, the pressure applied to the tissue tends to become less relevant whereas the gap distance between the electrically conductive surfaces becomes more significant for effective sealing. In other words, the chances of the two electrically conductive surfaces touching during activation increases as the vessels become smaller.

As mentioned above, in order to properly and effectively seal larger vessels, a greater closure force between opposing jaw members is required. It is known that a large closure force between the jaws typically requires a large moment about the pivot for each jaw. This presents a challenge because the jaw members are typically affixed with pins which are positioned to have a small moment arms with respect to the pivot of each jaw member. A large force, coupled with a small moment arm, is undesirable because the large forces may shear the pins. As a result, designers must compensate for these large closure forces by either designing instruments with metal pins and/or by designing instruments which at least partially offload these closure forces to reduce the chances of mechanical failure. As can be appreciated, if metal pivot pins are employed, the metal pins must be insulated to avoid the pin acting as an alternate current path between the jaw members which may prove detrimental to effective sealing.

Increasing the closure forces between electrodes may have other undesirable effects, e.g., it may cause the opposing electrodes to come into close contact with one another which may result in a short circuit or arcing between the electrodes, and a small closure force may cause pre-mature movement of the tissue during compression and prior to activation.

Thus, a need exists to develop an electrosurgical system which effectively seals vascular tissue and solves the aforementioned problems by providing an instrument which enables a large closure force between the opposing jaws members, reduces the chances of short circuiting the opposing jaws during activation and reduces the possibility of thermal spread.

SUMMARY

An electrosurgical system for sealing vessels using capacitive (RF) dielectric heating and a method thereof are provided. The present disclosure provides a system and method where tissue sealing is caused by capacitive heating, along with pressure and time. The system includes an electrosurgical tool or instrument having an end effector with parallel plate electrodes that will clamp onto a vessel, or tissue, and maintain a specified gap distance; however, the electrodes will be coated with a non-conductive dielectric material. Such an end effector will ensure that direct conduction between the electrodes does not occur through tissue or fluids and effectively creates a parallel plate capacitor with a dielectric, e.g., tissue and coating, in between the plates. The electrosurgical instrument will be activated with an AC signal at a specified RF frequency, e.g., a Debye resonance frequency, via an electrosurgical generator. An effective AC current will flow through the tissue and cause heating due to frictional losses from rotating polar molecules in the tissue.

Advantageously, the capacitive RF dielectric system of the present disclosure will provide more uniform heating, e.g., reduced thermal spread, due to a more uniform electric field generated between the electrodes than with a conventional ohmic heating system and will eliminate arcing since there will be no direct conduction between electrodes. Additionally, a more accurate temperature measurement is achieved with a single temperature sensor due to the uniform heat distribution. Furthermore, since the surface contacting tissue will be coated with a, preferably, non-stick, dielectric material, tissue sticking to the end effector will be reduced.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
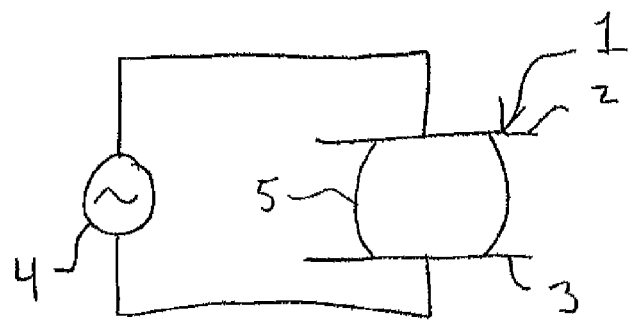
FIG. 1 is a schematic diagram illustrating the principles of one embodiment of the present disclosure.

Embodiments of the present disclosure will be described herein below with reference to the accompanying drawings. In the following description, well-known functions or constructions are not described in detail to avoid obscuring the disclosure in unnecessary detail. In the figures, like reference numerals represent like elements.

An electrosurgical system for sealing vessels using capacitive (RF) dielectric heating and a method thereof are provided. Capacitive RF dielectric heating is employed in an electrosurgical system to heat/desiccate tissue for sealing purposes. Generally, a high voltage RF frequency AC signal is applied to a set of parallel electrodes on opposite sides of a dielectric, e.g., tissue or electrode coatings, forming a capacitive circuit. A tissue to be sealed is sandwiched or placed between the electrodes so that an AC displacement current flows through the tissue as a result of polar molecules in the tissue aligning and rotating in opposite fashion to the applied AC electric field. Direct conduction does not occur but instead an effective AC current flows through the parallel electrodes due to polar molecules with effective charges rotating back and forth. Heating occurs because these polar molecules encounter interactions with neighboring molecules resulting in lattice and frictional losses as they rotate. Since the internal polar molecules of the tissue are being heated, the system does not rely on thermal conduction and does not require electrodes to contact a surface of the tissue as in conventional ohmic heating systems. The combination of the heat generated, along with pressure applied and a specified gap distance, will effectively seal the tissue held between the electrodes.

An exemplary electrical equivalent circuit of the principle described above is shown in FIG. 1 as a capacitor 1 having parallel electrodes 2, 3 coupled to an RF energy source 4, the parallel electrodes 2, 3 being placed around a medium 5, e.g., a dielectric, to be heated. Voltage losses of the dielectric increase as the frequency of the applied signal is increased due to higher speed interactions with the neighboring molecules. The higher the frequency of the alternating field the greater the energy imparted into the medium 5, e.g. tissue, until the frequency is so high that the rotating molecules can no longer keep up with the external field due to lattice limitations. The frequency at which that occurs is called a "Debye resonance" and is the frequency at which the maximum energy can be imparted into a medium for a given electric field strength and, therefore, the maximum heating. This high frequency limitation is inversely proportional to the complexity of the polar molecule. For example, proteins with amino acid polar side groups or chains have a slower rotation limitation, and thus lower Debye resonance, than simple polar water molecules. These Debye resonance frequencies also shift with temperature as the medium 5 is heated.

In the electrosurgical system of the present disclosure, the RF frequency or composite signal of several RF frequencies are selected to correlate with the dominant Debye resonance frequency groups of the tissue that is being heated. These Debye resonances are dependent on the polar molecular makeup of the tissue and thus a plurality of tissue types may be researched for different Debye resonance frequencies to be stored in the electrosurgical system to appropriately heat a selected tissue.

The system is constructed to provide an AC RF signal displacement current at an RF frequency in the range of 3 MHz to 300 MHz. This range includes the HF (3 MHz to 30 MHz) and VHF (30 MHz to 300 MHz) frequencies in the lower regions of the radio frequency (RF) range. Superior results are achieved by operating in the frequency range of 3 MHz-30 MHz.

The frequency or composite frequency groups of the RF signal used in the electrosurgical system will track with and change with temperature to account for the fact that the Debye resonance frequencies of the polar molecular constituents of the tissue also shift with temperature.

It is contemplated that the RF signal power level and electric field strength can be adjusted automatically by a computer control system which changes the load current to control heating rates and account for different tissue types. The power level is controlled by measuring the current and field strength across the load. The voltage (AC field strength) is then adjusted, which in turn varies the current, until measurements of the current and field strength indicate that the desired power level has been achieved.

Figure 2:
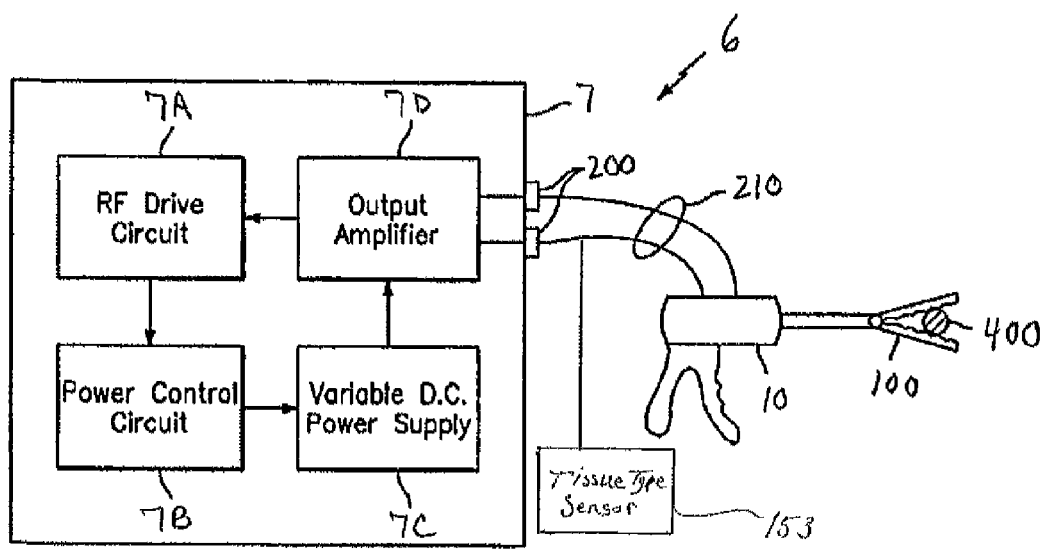
FIG. 2 is a simplified block diagram of an electrosurgical system which may be used with the present disclosure.

An electrosurgical system 6, which can be used to practice this disclosure, is shown in FIG. 2. The system 6 can be used for sealing vessels 400 and other tissues including ducts, veins, arteries and vascular tissue. The system 6 includes an electrosurgical generator 7 and a surgical tool, also referred to herein as a surgical instrument 10. The surgical instrument 10 is illustrated by way of example, and as will become apparent from the discussion below, other instruments can be utilized. The electrosurgical generator 6 includes several interconnected sub-units, including an RF drive circuit 7A, a power control circuit 7B, a variable D.C. power supply 7C and an output amplifier 7D. The surgical instrument 10 is electrically connected to the electrosurgical generator 7 using a plug 200 for receiving controlled electrosurgical power therefrom. The surgical instrument 10 has some type of end effector member 100, such as a forceps or hemostat, capable of grasping and holding the vessels and tissues of the patient. The member 100, also referred to simply as end effector 100, is assumed, in this embodiment, to be capable of applying and maintaining a relatively constant level of pressure on the vessel 400.

The member 100 is provided in the form of bipolar electrosurgical forceps using two generally opposing electrodes disposed on inner opposing surfaces of the member 100, and which are both electrically coupled to the output of the electrosurgical generator 7. During use, different electric potentials are applied to each electrode. When the forceps are utilized to clamp or grasp the vessel 400 therebetween, the electrical energy output from the electrosurgical generator 7 is transferred through the intervening tissue. Both open surgical procedures and endoscopic surgical procedures can be performed with suitably adapted surgical instruments 10. It should also be noted that the member 100 could be monopolar forceps that utilize one active electrode, with the other (return) electrode or pad being attached externally to the patient, or a combination of bipolar and monopolar forceps.

Figure 3:
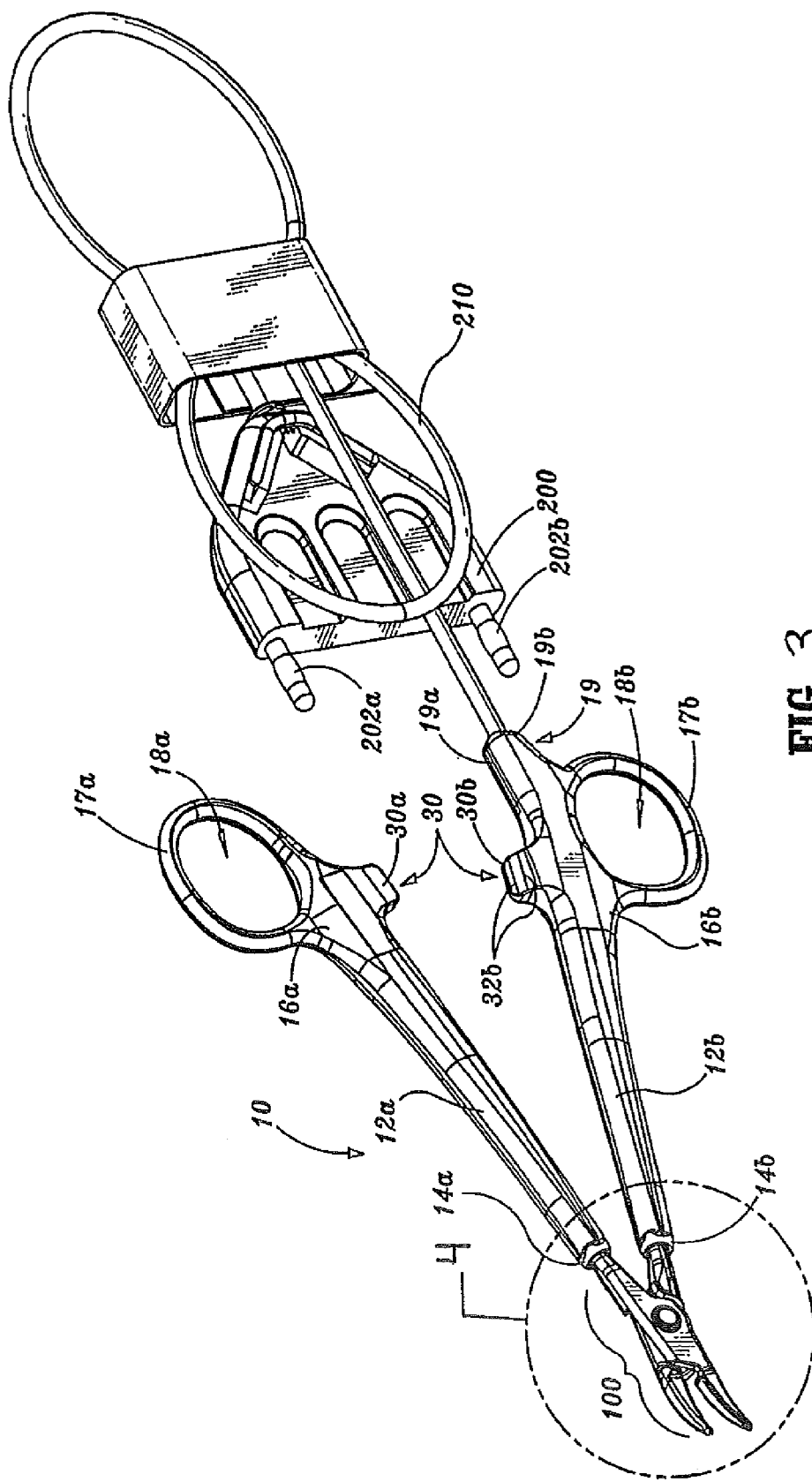
FIG. 3 is a perspective view of one embodiment of a surgical instrument having bipolar forceps which may be configured according to the present disclosure.
Figure 4:
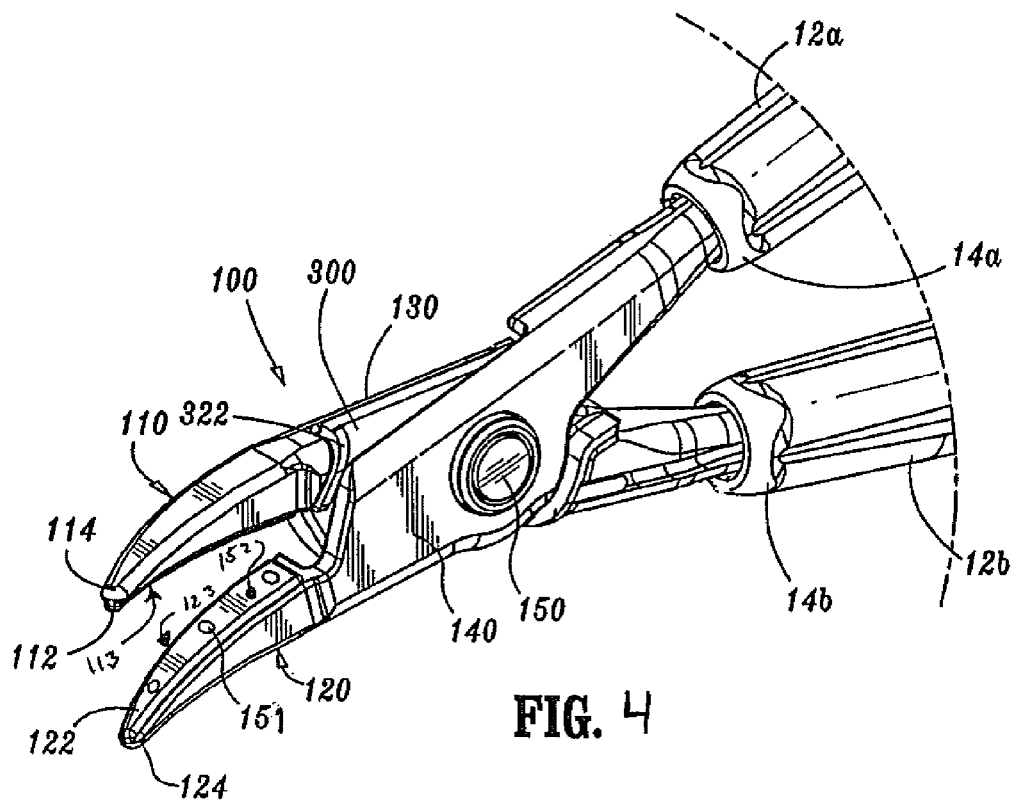
FIG. 4 is an enlarged, perspective view of the end effector assembly of the forceps of FIG. 3 shown in an open configuration.
Figure 5:
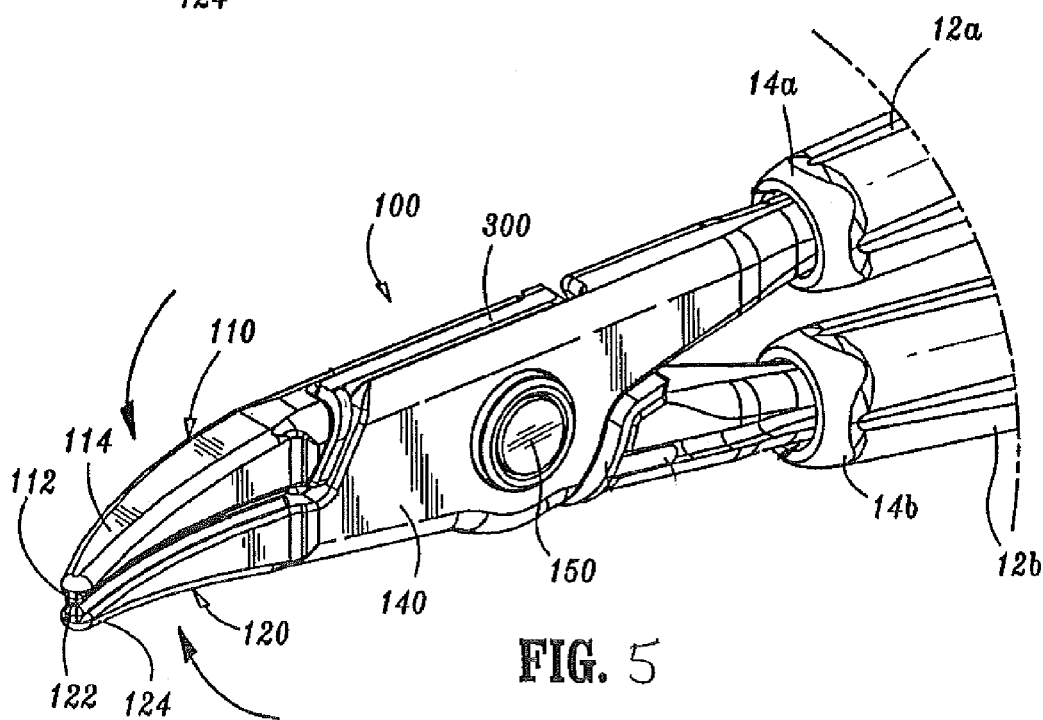
FIG. 5 is an enlarged, perspective view of the end effector assembly of the forceps of FIG. 3 shown in a closed configuration.

By way of further explanation, FIG. 3 is a perspective view of one embodiment of the surgical instrument 10 having a bipolar end effector implemented as forceps 100 while FIGS. 4 and 5 are enlarged, perspective views of a distal end of the bipolar forceps 100 shown in FIG. 3.

Referring now to FIGS. 3-6, a forceps 10 for use with open surgical procedures includes elongated shaft portions 12a and 12b each having a proximal end 16a and 16b, respectively, and a distal end 14a and 14b, respectively. In the drawings and in the descriptions which follow, the term "proximal", as is traditional, will refer to the end of the forceps 10 which is closer to the user, while the term "distal" will refer to the end which is further from the user.

The forceps 10 includes an end effector assembly 100 which attaches to distal ends 14a and 14b of shafts 12a and 12b, respectively. As explained in more detail below, the end effector assembly 100 includes pair of opposing jaw members 110 and 120 which are pivotably connected about a pivot pin 150.

Preferably, each shaft 12a and 12b includes a handle 17a and 17b disposed at the proximal end 16a and 16b thereof which each define a finger hole 18a and 18b, respectively, therethrough for receiving a finger of the user. As can be appreciated, finger holes 18a and 18b facilitate movement of the shafts 12a and 12b relative to one another which, in turn, pivot the jaw members 110 and 120 from an open position (FIG. 4) wherein the jaw members 110 and 120 are disposed in spaced relation relative to one another to a clamping or closed position (FIG. 5) wherein the jaw members 110 and 120 cooperate to grasp tissue 400 (FIG. 6) therebetween.

Figure 6:
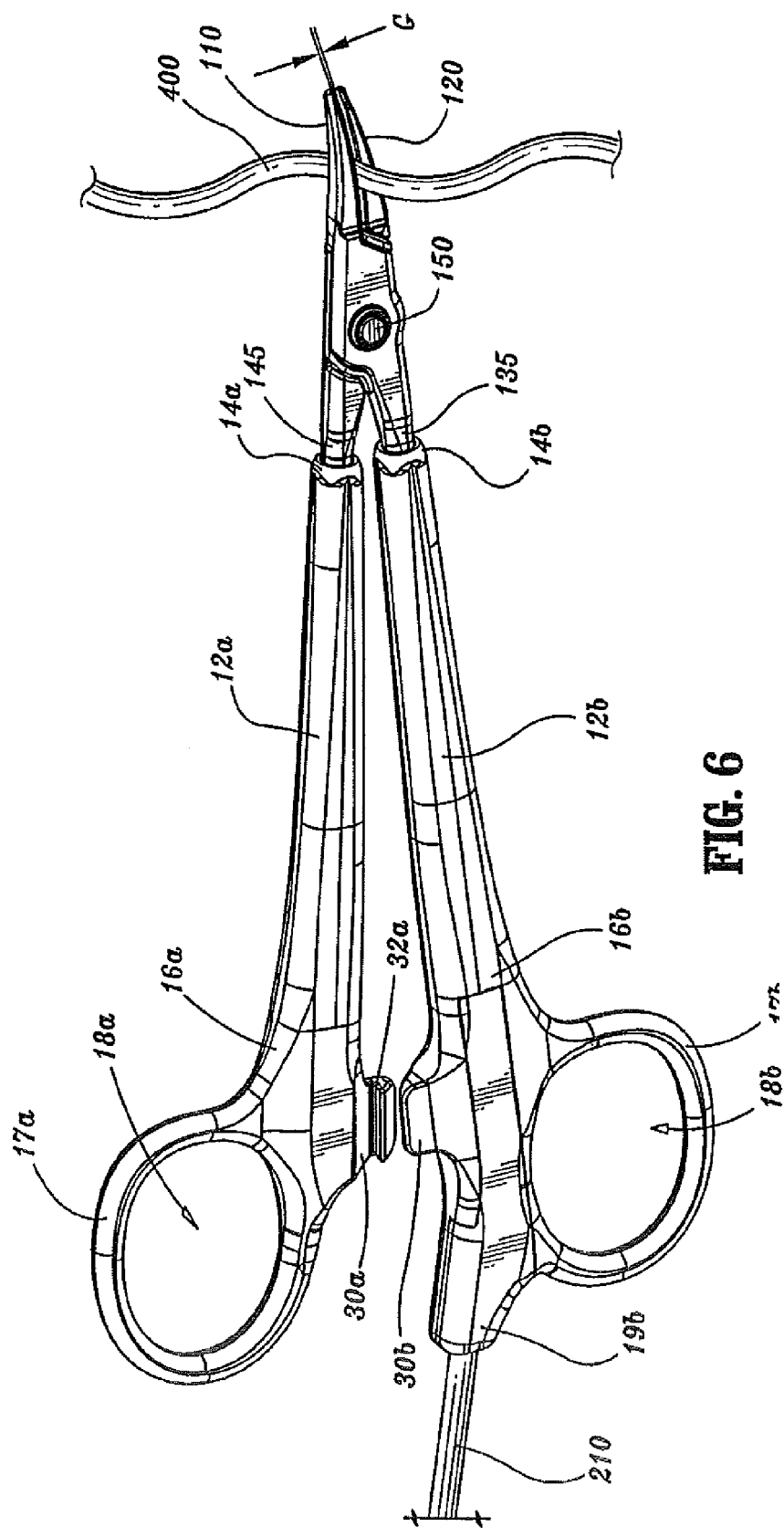
FIG. 6 is a right, perspective view of the forceps of FIG. 3 shown grasping tissue.

A ratchet 30 is preferably included for selectively locking the jaw members 110 and 120 relative to one another at various positions during pivoting. As best shown in FIG. 6, a first ratchet interface, e.g., 30a, extends from the proximal end 16a of shaft member 12a towards a second ratchet interface 30b in a generally vertically aligned manner such that the inner facing surfaces of each ratchet 30a and 30b abut one another upon closure about the tissue 400. Preferably, each ratchet interface 30a and 30b includes a plurality of flanges 32a and 32b, respectively, which project from the inner facing surface of each ratchet interface 30a and 30b such that the ratchet interfaces 30a and 30b interlock in at least one position. In the embodiment shown in FIG. 6, the ratchet interfaces 30a and 30b interlock at several different positions.

Preferably, each position associated with the cooperating ratchet interfaces 30a and 30b holds a specific, i.e., constant, strain energy in the shaft members 12a and 12b which, in turn, transmits a specific closing force to the jaw members 110 and 120. It is envisioned that the ratchet 30 may include graduations or other visual markings which enable the user to easily and quickly ascertain and control the amount of closure force desired between the jaw members. A design without a ratchet system or similar system would require the user to hold the jaw members 110 and 120 together by applying constant force to the handles 17a and 17b which may yield inconsistent results.

As best illustrated in FIG. 3, one of the shafts, e.g., 12b, includes a proximal shaft connector 19 which is designed to connect the forceps 10 to a source of electrosurgical energy such as an electrosurgical generator 7, which will be described below in detail. More particularly, proximal shaft connector 19 is formed by a cover 19a and a flange 19b which extends proximally from shaft 12b. Preferably, cover 19a and flange 19b mechanically cooperate to secure an electrosurgical cable 210 to the forceps 10 such that the user may selectively apply electrosurgical energy as needed.

The proximal end of the cable 210 includes a plug 200 having a pair of prongs 202a and 202b which are dimensioned to electrically and mechanically engage the electrosurgical energy generator. The interior of cable 210 houses at least a pair of leads which conduct the different electrical potentials from the electrosurgical generator to the jaw members 110 and 120. The cable 210 may also include a plurality of other leads coupled to sensors, e.g., a temperature sensor, voltage sensor, current sensor, tissue type sensor, etc., for providing feedback to the electrosurgical generator 7, as explained in greater detail below. FIG. 2 shows a tissue type sensor 153 for determining a type of tissue to be sealed coupled to the generator 7 via cable 210 to provide tissue type feedback to the generator as will be described below.

As best seen in FIGS. 4 and 5, the two opposing jaw members 110 and 120 of the end effector assembly 100 are pivotable about pin 150 from the open position to the closed position for grasping tissue 400 therebetween. Jaw members 110 and 120 are generally symmetrical and include similar component features which cooperate to permit facile rotation about pivot pin 150 to effect the grasping and sealing of tissue 400. As a result and unless otherwise noted, jaw member 110 and the operative features associated therewith will initially be described herein in detail and the similar component features with respect to jaw member 120 will be briefly summarized thereafter.

Jaw member 110 includes an insulated outer housing 114 which is dimensioned to mechanically engage an electrode 112 and a proximally extending flange 130 which is dimensioned to seat a distal connector 300. Preferably, outer insulative housing 114 extends along the entire length of jaw member 110 to reduce alternate or stray current paths during sealing and/or incidental burning of tissue 400. The inner facing surface of flange 130 includes an electrically conductive plate which conducts electrosurgical energy to the electrode 112 upon activation.

Likewise, jaw member 120 include similar elements which include: an outer housing 124 which engages an electrode 122; a proximally extending flange 140 which seats the opposite face of the distal connector 300; an electrically conductive plate which conducts electrosurgical energy to the electrode 122 upon activation.

Each electrode 112, 122 of the first and second jaw members will be coated with a non-conductive dielectric material 113, 123 that itself will not be heated since the dielectric material will be selected to have a Debye resonance at much higher frequency then a Debye resonance of the tissue to be sealed. Advantageously, the dielectric material will increase the dielectric constant of the gaps between the electrodes 112, 122 and the tissue 400 to be heated thus improving energy transfer to the tissue 400.

Preferably, the dielectric material 113, 123 is molded onto the jaw members 110, 120 (e.g., overmolding, injection molding, etc.), stamped onto the jaw members 110, 120 or deposited (e.g., deposition) onto the jaw members 110, 120. The dielectric material may also be pre-formed and slideably attached to the jaw members and/or attached to the electrodes 112, 112 in a snap-fit manner. Other techniques involve thermally spraying the dielectric material onto the surface of the jaw member 110, 120. Alternatively, the dielectric material 113, 123 can be molded onto the inner-facing surface of the jaw members 110, 120 or, in some cases, it may be preferable to adhere the dielectric material to the inner facing surfaces of the jaw members 110, 120 by any known method of adhesion.

Preferably, the dielectric material is a material having superior non-stick properties, for example, KAPTON®, polytetrafluoroethylene (PTFE), etc, which will reduce the amount of tissue that sticks to the end effector and thus improves the overall efficacy of the instrument. KAPTON® is a polyimide film commercially available from Dupont of Wilmington, Del.

Since the Debye resonance frequency of the tissue will shift with a change in temperature of the tissue, the end effector 100 will include at least one temperature sensor 152. The temperature sensor 152 may be any known temperature sensor in the art, for example, a thermocouple, thermistor, resistance temperature detector (RTD), semiconductor temperature device, infrared temperature sensor, etc. The temperature sensor 152 will be coupled to the generator 7 via cable 210 to provide temperature feedback to the generator as will be described below.

It is envisioned that one of the jaw members, e.g., 120, includes at least one stop member 151 disposed on an inner facing surface of the electrode surface 112 (and/or 122). Alternatively or in addition, the stop member 151 may be positioned adjacent to the electrode 112, 122 or proximate the pivot pin 150. The stop member(s) is preferably designed to facilitate gripping and manipulation of tissue 400 and to define a gap "G" (FIG. 6) between opposing jaw members 110 and 120 during sealing. Preferably the separation distance during sealing or the gap distance "G" is within the range of about 0.001 inches (~0.03 millimeters) to about 0.006 inches (~0.16 millimeters).

A detailed discussion of these and other envisioned stop members 151 as well as various manufacturing and assembling processes for attaching, disposing, depositing and/or affixing the stop members 151 to the electrodes surfaces 112, 122 are described in commonly-assigned, co-pending PCT Application Serial No. PCT/U.S.01/11222 entitled "BIPOLAR ELECTROSURGICAL FORCEPS WITH NON-CONDUCTIVE STOP MEMBERS" which is hereby incorporated by reference in its entirety herein.

Figure 7:
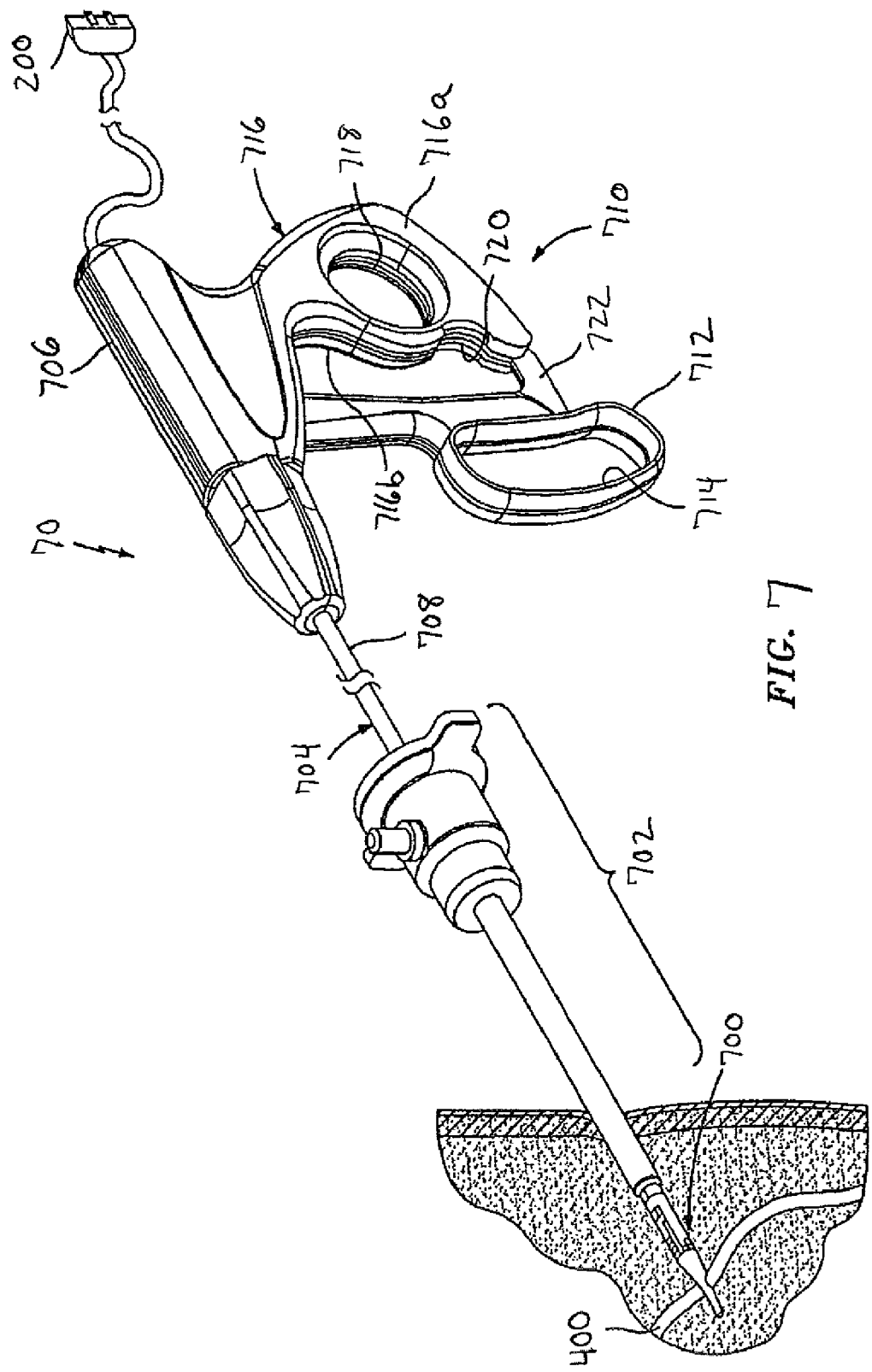
FIG. 7 is a perspective view of an endoscopic forceps which may be configured according to the present disclosure.

FIG. 7 is a perspective view of another embodiment of a surgical instrument 70 having end effector members or forceps 700 that are suitable for an endoscopic surgical procedure. The end effector member 700 is depicted as sealing the tubular vessel 400 through a cannula assembly 702.

The surgical instrument 70 for use with endoscopic surgical procedures includes a drive rod assembly 704 which is coupled to a handle assembly 706. The drive rod assembly 704 includes an elongated hollow shaft portion 708 having a proximal end and a distal end. An end effector assembly 700 is attached to the distal end of shaft 708 and includes a pair of opposing jaw members. Preferably, handle assembly 706 is attached to the proximal end of shaft 708 and includes an activator 710 for imparting movement of the forceps jaw members of end effector member 700 from an open position, wherein the jaw members are disposed in spaced relation relative to one another, to a clamping or closed position, wherein the jaw members cooperate to grasp tissue therebetween.

Similar to end effector 100, end effector 700 will include first and second jaw members, each having an electrode for imparting electrosurgical energy to tissue 400. Each electrode will be coated with a non-conductive dielectric material as described above in reference to end effector 100. Alternatively, a non-conductive pad may be selectively mounted atop the inner facing surface of each electrode or the electrodes may be manufactured with the pad mounted thereon.

Activator 710 includes a movable handle 712 having an aperture 714 defined therein for receiving at least one of the operator's fingers and a fixed handle 716 having an aperture 718 defined therein for receiving an operator's thumb. Movable handle 712 is selectively moveable from a first position relative to fixed handle 716 to a second position in the fixed handle 716 to close the jaw members. Preferably, fixed handle 716 includes a channel 720 which extends proximally for receiving a ratchet 722 which is coupled to movable handle 712. This structure allows for progressive closure of the end effector assembly, as well as a locking engagement of the opposing jaw members. In some cases it may be preferable to include other mechanisms to control and/or limit the movement of handle 712 relative to handle 716 such as, e.g., hydraulic, semi-hydraulic and/or gearing systems. As with instrument 10, a stop is also provided to maintain a minimum gap between the jaw members.

The handle 716 includes handle sections 716a and 716b, and is generally hollow such that a cavity is formed therein for housing various internal components. For example, the cavity can house a PC board which controls the electrosurgical energy being transmitted from the electrosurgical generator 7 to each jaw member, via connector 200. More particularly, electrosurgical energy generated from the electrosurgical generator 7 is transmitted to the handle PC board by a cable 210. The PC board converts the electrosurgical energy from the generator into two different electrical potentials which are transmitted to each jaw member by a separate terminal clip. The handle 716 may also house circuitry that communicates with the generator 7, for example, identifying characteristics of the electrosurgical tool 70 for use by the electrosurgical generator 7, transmitting temperature values, transmitting calculated impedance values, etc.

A lost motion mechanism may be positioned between each of the handle sections 716a and 716b for maintaining a predetermined or maximum clamping force for sealing tissue between the jaw members. It is also contemplated that other endoscopic vessel sealing instruments may be utilized with the present disclosure such as the vessel sealer and dividers, e.g., the LIGASURE ATLAST™ and LIGASURE 5 mm™ manufactured and sold by VALLEYLAB, Inc—a division of TYCO HEALTH CARE GROUP, LP.

Having thus described two exemplary and non-limiting embodiments of surgical instruments 10, 70 that can be employed with the electrosurgical generator 7, a description will now be provided of various aspects of the presently disclosed electrosurgical generator 7.

Figure 8:
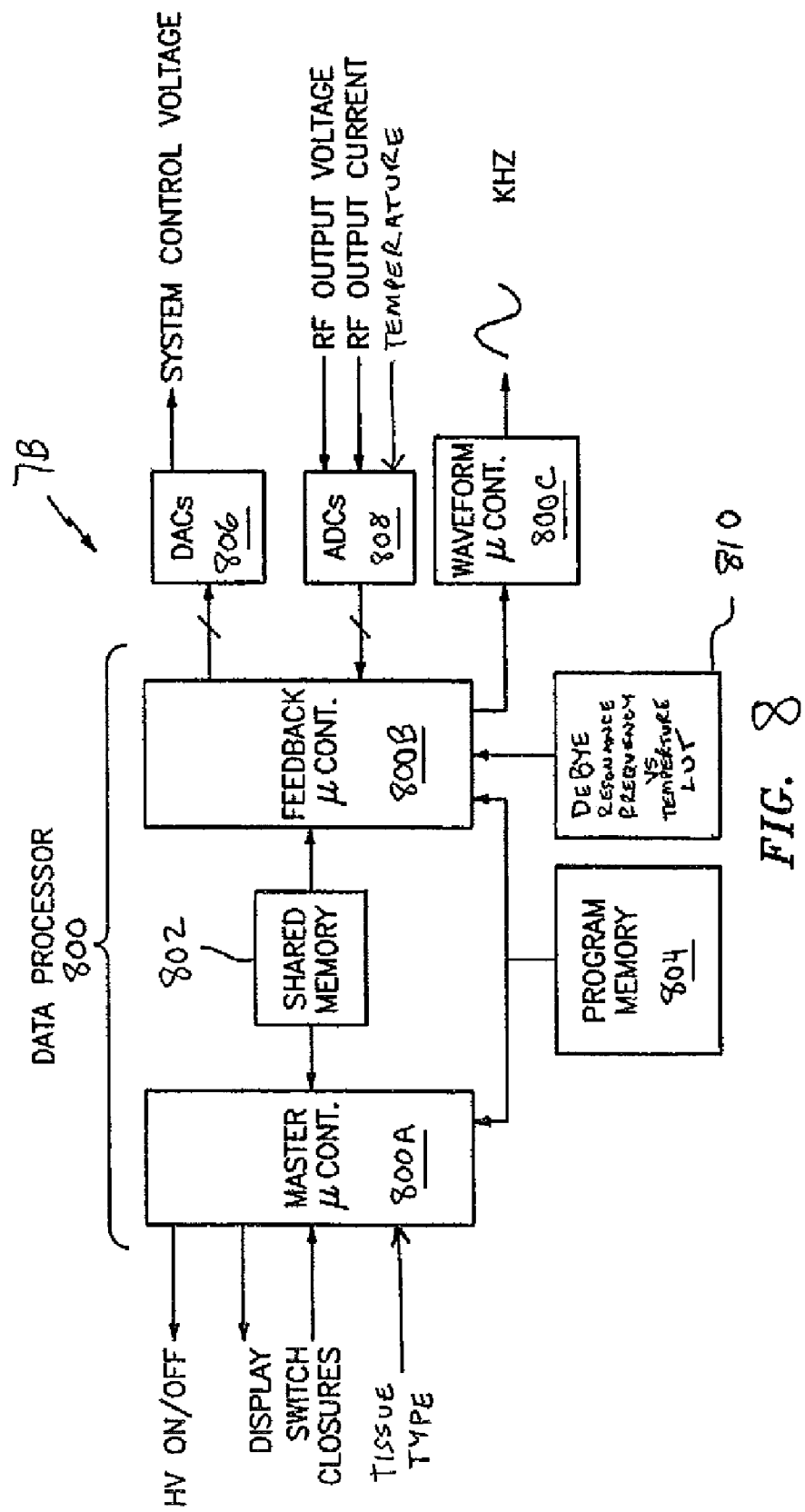
FIG. 8 is a simplified block diagram of one embodiment of a power control circuit for use with an electrosurgical generator.

FIG. 8 is a block diagram that illustrates the power control circuit 7B of FIG. 2 in greater detail. The power control circuit 7B includes a suitably programmed data processor 800 that is preferably implemented as one or more microcontroller devices. In one envisioned embodiment there are two principal microcontrollers, referred to as a main microcontroller 800A and a feedback microcontroller 800B. These two microcontrollers are capable of communicating using shared data that is stored and retrieved from a shared read/write memory 802, e.g., a RAM. A control program for the data processor 800 is stored in a program memory 804, and includes software routines and algorithms for controlling the overall operation of the electrosurgical generator 7. In general, the feedback microcontroller 800B has a digital output bus coupled to an input of a digital to analog converter (DAC) block 806 which outputs an analog signal. This is a system control voltage (SCV), which is applied to the variable DC power supply 7C to control the magnitude of the voltage and current of output RF pulses.

An analog to digital converter (ADC) block 808 receives analog inputs and sources a digital input bus of the feedback microcontroller 800B. Using the ADC block 808, the microcontroller 800B is apprised of the value of the actual output voltage and the actual output current, thereby closing the feedback loop with the SCV signal. The values of the output voltage and current can be used for determining tissue impedance and for the overall, general control of the applied RF energy waveform. It should be noted that at least the ADC block 808 can be an internal block of the feedback microcontroller 800B, and need not be a separate, external component. It should be further noted that the same analog signals can be digitized and read into the master microcontroller 800A, thereby providing redundancy. The master microcontroller 800A controls the state (on/off) of the high voltage (e.g., 190V max) power supply as a safety precaution, controls the front panel display(s), and also receives various input switch closures, such as a tissue type selected by an operator.

It is envisioned that a third (waveform) microcontroller 800C may be employed to generate a desired sinusoidal waveform at a specified Debye resonance frequency that forms the basis of the RF pulses applied to the tissue to be sealed, such as the vessel 400 (FIG. 6). The waveform microcontroller 800C is controlled by the feedback microcontroller 800B and is programmed thereby. Depending on the tissue type, e.g., either selected by the user or sensed via the end effector 100, the feedback controller 800B will access a Debye resonance frequency vs. temperature curve from lookup table (LUT) 810 and will load the appropriate curve from LUT 810. An output signal line from the feedback microcontroller 800B is coupled to an input of the waveform microcontroller 800C to essentially turn the waveform microcontroller 800C on and off to provide the pulsed RF signal in accordance with an aspect of this disclosure. This particular arrangement is, of course, not to be viewed in a limiting sense upon the practice of this system, as those skilled in the art may derive a number of methods and circuits for generating the desired RF pulses in accordance with the teachings found herein.

Furthermore, the ADC 808 will receive a signal indicative of a temperature of the tissue to be sealed and inputs the signal into the feedback microcontroller 800B. The feedback microcontroller 800B will then again access the LUT 810 to determine a shift in the Debye resonance frequency of the tissue selected.

Alternatively, the shift in the Debye resonance frequency of the tissue selected may be determined by a predictive algorithm stored in program memory 804. The predictive algorithm will determine the shift in the Debye resonance frequency from a table derived from experimental data for various tissue types.

Figure 9:
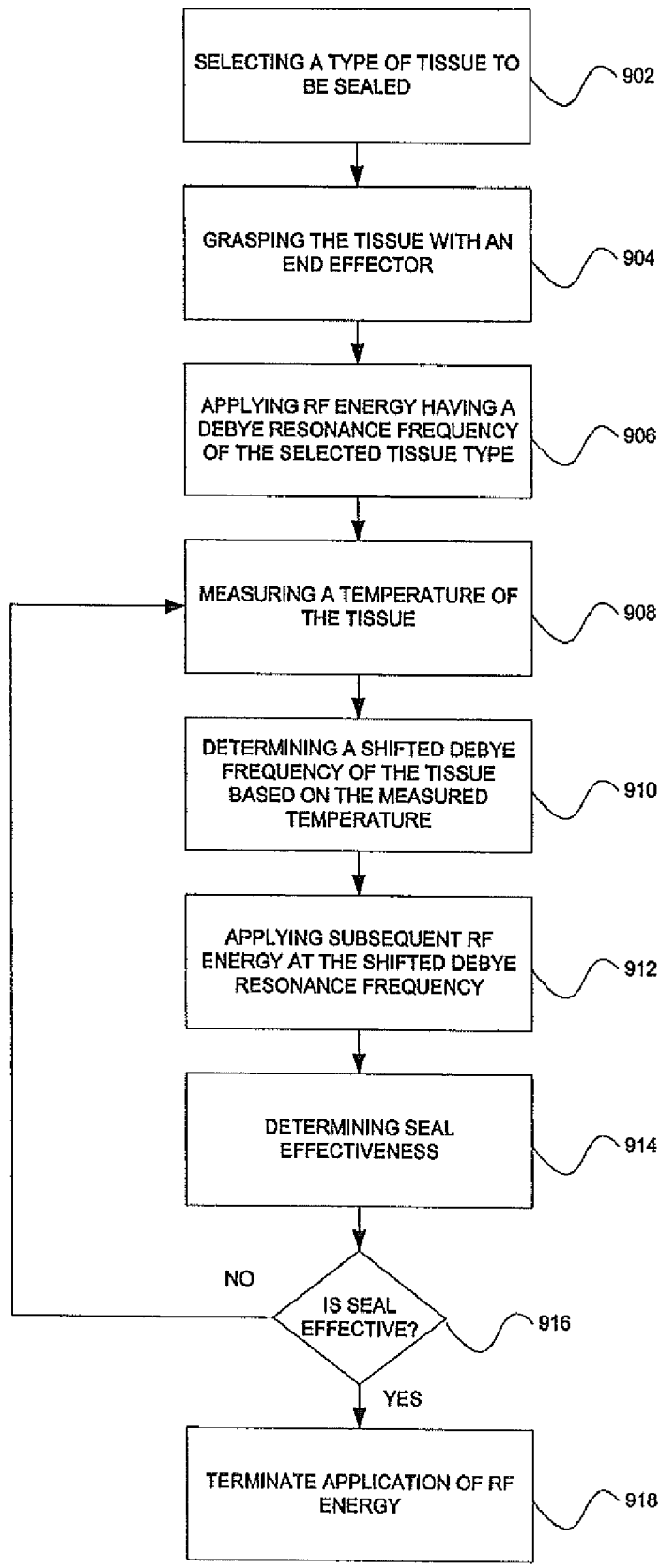
FIG. 9 is a flowchart illustrating one method for sealing tissue according to the present disclosure.

Referring to FIG. 9, a method for electrosurgically sealing tissue using capacitive RF dielectric heating is illustrated. In step 902, a type of tissue to be sealed is determined and selected either manually or automatically by the electrosurgical generator 7. An electrosurgical instrument 10 having an end effector 100 including electrodes having a non-conductive dielectric material disposed thereon is electrically coupled to generator 7 and employed to grasp the tissue to be sealed at the operative site, step 904. The generator will load the appropriate Debye resonance frequency curve based on the type of tissue selected. The generator 7 via waveform generator 800C will apply RF energy at the appropriate Debye resonance frequency to the end effector 100, step 906.

Since the optimal Debye resonance frequency will shift with a change in temperature, temperature sensor 152 will continuously measure the temperature of the tissue to be sealed, in step 908. The temperature will be feedback to the generator 7 via feedback controller 800B and will determine a shifted Debye resonance frequency via the Debye resonance frequency curve for the tissue selected, in step 910. In step 910, the generator 7 will apply subsequent RF energy at the shifted Debye resonance frequency. Alternatively, the shifted Debye resonance frequency will be determined by the predictive algorithm described above.

In step 914, the generator 7 will determine the effectiveness of the seal by determining the impedance of the tissue. The impedance may be determined by sensing the current and voltage of the tissue and calculating the impedance via the appropriate algorithm as is known in the art. In step 916, if the generator 7 determines the seal is effective, the generator will terminate application of the RF energy (step 918) and, optionally, provide an indication to the user that the tissue is sealed. Otherwise, if the seal is not effective, the method will return to step 908 and repeat steps 908 through 916 until it is determines the seal is effective.

It is envisioned that by utilizing a capacitive system for heating, and thus sealing tissue, more uniform heating will be achieved due to the uniform electric field generated between the electrodes of the end effector. Additionally, since the electrodes of the end effector will act as a pure capacitor, there will be no resistive component through the tissue and, therefore, no current which will eliminate the possibility of arcing. Furthermore, since the dielectric material of the end effector will be selected to have superior non-stick properties, the amount of tissue sticking to the end effector will be eliminated or reduced, thus, improving the overall efficacy of the system.

While several embodiments of the disclosure have been shown in the drawings, it is not intended that the disclosure be limited thereto, as it is intended that the disclosures be as broad in scope as the art will allow and that the specification be read likewise. Therefore, the above description should not be construed as limiting, but merely as exemplifications of preferred embodiments.

What is claimed is:

1. A method for electrosurgically sealing tissue, the method comprising the steps of:
   selecting a type of tissue to be sealed;
   determining a predetermined frequency based on the type of tissue to be sealed;
   executing a predictive algorithm to determine a shift in the predetermined frequency; and
   applying RF energy to the tissue at the shifted predetermined frequency determined by the predictive algorithm.

2. The method according to claim 1, wherein the predetermined frequency is a Debye resonance frequency of the tissue to be sealed.

3. The method according to claim 1, wherein the applying step includes generating an AC electric field that causes energy to flow at the predetermined frequency through the tissue to be sealed.

4. The method according to claim 1, wherein the applying step includes applying RF energy to the tissue via an end effector having opposing jaw members adapted to connect to a source of electrosurgical energy.

5. The method according to claim 4, wherein each jaw member includes an electrode having a dielectric coating, wherein the dielectric coating has a predetermined frequency different than the predetermined frequency of the tissue.

6. A method for electrosurgically sealing tissue, the method comprising the steps of:
   selecting a type of tissue to be sealed;
   determining a Debye resonance frequency of the tissue being sealed based on the type of tissue to be sealed;
   applying RF energy to the tissue, the RF energy being applied at the Debye resonance frequency of the tissue being sealed;
   executing a predictive algorithm to determine a shift in the Debye resonance frequency of the tissue being sealed; and
   regulating the application of RF energy to the tissue to cause energy to flow through the tissue being sealed at the shifted Debye resonance frequency based on the determined shift.

7. A method according to claim 6, wherein the applying step includes generating an AC electric field that causes energy to flow at the Debye resonance frequency through the tissue to be sealed.

8. The method according to claim 6, further comprising the step of:
   providing an electrosurgical instrument for sealing tissue, the electrosurgical instrument comprising:
     an end effector having opposing jaw members, at least one of the jaw members movable relative to one another from a first position wherein the jaw members are disposed in spaced relation relative to one another to a second position wherein the jaw members cooperate to grasp tissue therebetween, at least one jaw member adapted to connect to a source of electrosurgical energy;
   grasping tissue between the jaw members; and
   applying RF energy to the grasped tissue at the Debye resonance frequency of the tissue.

9. A method for electrosurgically sealing tissue, the method comprising the steps of:
   providing an electrosurgical instrument for sealing tissue, the electrosurgical instrument comprising:
     an end effector having opposing jaw members, at least one of the jaw members movable relative to one another from a first position wherein the jaw members are disposed in spaced relation relative to one another to a second position wherein the jaw members cooperate to grasp tissue therebetween, at least one jaw member adapted to connect to a source of electrosurgical energy;
   selecting a type of tissue to be sealed;
   determining a predetermined frequency based on the type of tissue to be sealed;
   applying RF energy from the source of electrosurgical energy to the tissue via the jaw members, the RF energy applied at the predetermined frequency;
   executing a predictive algorithm to determine a shift in the predetermined frequency of the tissue being sealed; and
   regulating the application of RF energy from the electrosurgical energy source to the tissue to cause energy to flow through the tissue being sealed at the shifted predetermined frequency based on the determined shift.

10. The method according to claim 9, wherein the predetermined frequency is a Debye resonance frequency of the tissue to be sealed.

* * * * *